US012582680B2

(12) United States Patent　　(10) Patent No.: US 12,582,680 B2
Ito et al.　　(45) Date of Patent: Mar. 24, 2026

(54) PHARMACEUTICAL COMPOSITION FOR PREVENTION, AMELIORATION, OR TREATMENT OF SKIN DISEASE

(71) Applicants: RIKEN, Wako (JP); KEIO UNIVERSITY, Tokyo (JP)

(72) Inventors: Yoshihiro Ito, Wako (JP); Kenya Honda, Wako (JP); Masayuki Amagai, Tokyo (JP); Eiryo Kawakami, Wako (JP)

(73) Assignees: RIKEN, Tokyo (JP); KEIO UNIVERSITY, Tokyo (JP)

( * ) Notice: Subject to any disclaimer, the term of this patent is extended or adjusted under 35 U.S.C. 154(b) by 797 days.

(21) Appl. No.: 17/427,988

(22) PCT Filed: Feb. 3, 2020

(86) PCT No.: PCT/JP2020/003957

§ 371 (c)(1),
(2) Date: Aug. 3, 2021

(87) PCT Pub. No.: WO2020/162405

PCT Pub. Date: Aug. 13, 2020

(65) Prior Publication Data

US 2022/0023355 A1　　Jan. 27, 2022

(30) Foreign Application Priority Data

Feb. 4, 2019　(JP) ................................. 2019-017882

(51) Int. Cl.

| | |
|---|---|
| *A61K 35/74* | (2015.01) |
| *A01K 67/0276* | (2024.01) |
| *A61P 17/00* | (2006.01) |
| *C12N 1/20* | (2006.01) |
| *C12N 1/205* | (2026.01) |
| *C12R 1/44* | (2006.01) |

(52) U.S. Cl.

CPC .............. *A61K 35/74* (2013.01); *A61P 17/00* (2018.01); *C12N 1/205* (2021.05); *A01K 67/0276* (2013.01); *A01K 2217/075* (2013.01); *A01K 2227/105* (2013.01); *C12R 2001/44* (2021.05)

(58) Field of Classification Search

CPC ...... A23L 33/135; A23L 33/17; A23L 33/185; A61K 35/747; A61K 35/74; A61P 1/00; A61P 17/00; A61P 17/04; A61P 17/06; C12N 1/205; C12N 1/20; A01K 2217/075; C12R 2001/44; G01N 2800/202; C12Q 1/14

See application file for complete search history.

(56) References Cited

U.S. PATENT DOCUMENTS

| | | | | |
|---|---|---|---|---|
| 9,113,636 | B2 * | 8/2015 | von Maltzahn | ........ A01N 63/20 |
| 2006/0140972 | A1 * | 6/2006 | Alm | ........................ C07K 14/31 |
| | | | | 435/6.15 |
| 2016/0143962 | A1 * | 5/2016 | Berry | ................... A61K 9/0031 |
| | | | | 424/93.3 |
| 2018/0289751 | A1 | 10/2018 | Nakatsuji et al. | |
| 2019/0010487 | A1 * | 1/2019 | Holmberg | .......... G01N 33/5308 |
| 2019/0321416 | A1 * | 10/2019 | Wagner | ................... A61K 35/74 |

FOREIGN PATENT DOCUMENTS

| | | | | |
|---|---|---|---|---|
| CN | 107735098 | A | 2/2018 | |
| CN | 108048361 | A | 5/2018 | |
| JP | 2006-342147 | A | 12/2006 | |
| JP | 2011200211 | A * | 10/2011 | |
| JP | 2018-515488 | A | 6/2018 | |
| KR | 2014-0010578 | A | 1/2014 | |
| WO | 81/00962 | A1 | 4/1981 | |
| WO | 2014/210372 | A1 | 12/2014 | |
| WO | WO-2015100432 | A2 * | 7/2015 | ............. A01H 17/00 |
| WO | 2016/086209 | A1 | 6/2016 | |
| WO | 2016/179440 | A2 | 11/2016 | |
| WO | 2018/156916 | A2 | 8/2018 | |
| WO | 2019/017389 | A1 | 1/2019 | |
| WO | 2019/204475 | A1 | 10/2019 | |

OTHER PUBLICATIONS

JP2011200211A: New lactic acid bacterium, and medicine, food and drink, and fodder containing the new lactic acid bacterium ( Year: 2010).*

Jahns et al. Anaerobe 38 (2016) 47e49; Microbial colonization of normal skin: Direct visualization of 194 skin biopsies (Year: 2016).*

Gonzales et al, J Allergy Clin Immunol (Jan. 2017) (Year: 2017).*

Kennedy et al, Curr Allergy Asthma Rep (2017) 17: 81 (Year: 2017).*

Bacterial Metabolism By G. Gottschalk, p. 8 (Year: 1979).*

Eye Wash, dailymed.nlm.nih.gov, NDC Code: 67510-0662-4, (Feb. 22, 2013) (Year: 2013).*

Note for guidance on quality of water for pharmaceutical use. European Medicines Agency. 2002, Reference No. CPMP/QWP/158/01 Revision; https://www.ema.europa.eu/en/quality-water-pharmaceutical-use-scientific-guideline (Year: 2002).*

SCV Search Results Details for U.S. Appl. No. 17/427,988 (Year: 2024).*

WO2016086208 SEQ file from PatentScope. relevant sequence data. (Year: 2016).*

(Continued)

*Primary Examiner* — Kade Ariani

(74) *Attorney, Agent, or Firm* — WHDA, LLP

(57) ABSTRACT

In the present invention, the influence by flora of the skin on dermatitis is examined by analyzing Tmem79-knockout model mice, and a bacterium having a suppressive effect on dermatitis is identified, and the present invention relates to a pharmaceutical composition derived from such a bacterium, containing as active components one or more substances selected from: (a) a bacterial cell of an ampicillin-sensitive bacterium, or a constituent component of the bacterium; (b) a culture supernatant of an ampicillin-sensitive bacterium, or a purified product from the culture supernatant; (c) an extract of an ampicillin-sensitive bacterium; and (d) a metabolite of an ampicillin-sensitive bacterium.

3 Claims, 30 Drawing Sheets

Specification includes a Sequence Listing.

(56) References Cited

OTHER PUBLICATIONS

BLAST sequence Alignment result (Year: 2025).*
Ito, Y. et al., "Mutualistic skin bacteria protect against dermatitis via the induction of steroid biosynthesis pathways", Journal of Investigative Dermatology, Sep. 4, 2019, vol. 139, Issue 9, Supplement, p. S272; Cited in ISR. (4 pages).
Nakatsuji, et al., "Antimicrobials from human skin commensal bacteria protect against *Staphylococcus aureus* and are deficient in atopic dermatitis", Sci. Transl. Med., Feb. 22, 2017, 9(378), eaah4680; Cited in the Specification. (12 pages).
Kennedy, et al., "Skin microbiome before development of atopic dermatitis: Early colonization with commensal staphylococci at 2 months is associated with a lower risk of atopic dermatitis at 1 year", J. Allergy Clin. Immunol., Jan. 2017; 139(1), pp. 166-172; Cited in the Specification. (7 pages).
Japanese Journal of Clinical Immunology, 2014, 37(4), p. 370b; Cited in the Specification. (1 page).
Saunders, et al., "Tmem79/Matt is the matted mouse gene and is a predisposing gene for atopic dermatitis in human subjects", J. Allergy Clin. Immunol. Nov. 2013; 132(5), pp. 1121-1129; Cited in the Specification. (9 pages).
Fits, et al., "Imiquimod-Induced Psoriasis-Like Skin Inflammation in Mice Is Mediated via the IL-23/IL-17 Axis", J Immunol. May 1, 2009;182(9), pp. 5836-5845; Cited in the Specification. (11 pages).
International Search Report dated Apr. 28, 2020, issued in counterpart Application No. PCT/JP2020/003957, with English Translation provided from WIPO. (15 pages).
Written Opinion dated Apr. 28, 2020, issued in counterpart Application No. PCT/JP2020/003957, with English Translation provided from WIPO. (30 pages).
Office Action dated Oct. 20, 2023, issued in counterpart TW Application No. 109103376, with English translation provided by Louis International Patent Office. (11 pages).

Yantera et al., *Staphylococcus cons* for use in the treatment of burn wound infections, Journal of Mussurea National Infectology, Jan. 2000, vol. 10, No. 5, pp. 393-394; cited in CN Office Action dated Aug. 25, 2023.
Office Action dated Oct. 16, 2023, issued in counterpart CA Application No. 3128357. (5 pages).
Office Action dated Aug. 25, 2023, issued in counterpart CN Application No. 202080012405.0 with English translation. (13 pages).
Office Action dated Sep. 19, 2023, issued in counterpart JP Application No. 2020-571188 with English translation. (6 pages).
Extended (Supplementary) European Search Report dated Dec. 12, 2023, issued in counterpart EP Application No. 20753095.7. (127 pages).
Office Action dated Jul. 4, 2023, issued in counterpart JP application No. 2020-571188, with English translation provided by Japanese Patent Office. (10 pages).
Office Action dated Oct. 20, 2023, issued in counterpart TW Application No. 109103376, with English translation. (11 pages).
Office Action dated Apr. 23, 2024, issued in counterpart CN application No. 202080012405.0, with English translation. (16 pages).
Extended (Supplementary) European Search Report dated Dec. 12, 2023, issued in counterpart EP application No. 20753095.7. (9 pages).
Office Action dated Nov. 14, 2024, issued in counterpart CA application No. 3128357. (4 pages).
Chang, C. et al., Community-Acquired Klebsiella pneumoniae Complicated Skin and Soft-Tissue Infections of Extremities: Emphasis on Cirrhotic Patients and Gas Formation, Infection, vol. 36, No. 4, p. 328-334, 2008 (7 pages); Cited in AU Office Action dated Sep. 30, 2025.
Office Action dated Sep. 30, 2025, issued in counterpart AU Application No. 2020218984. (9 pages).
Office Action dated Dec. 15, 2025, issued in counterpart CA Application No. 3,128,357. (5 pages).

* cited by examiner

[Fig. 1]

Fig.2
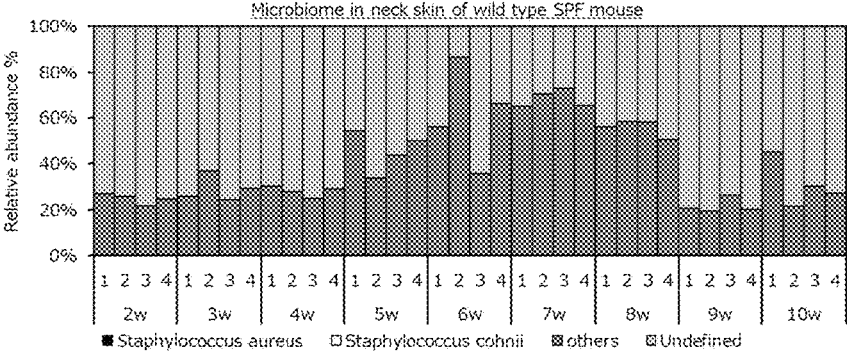
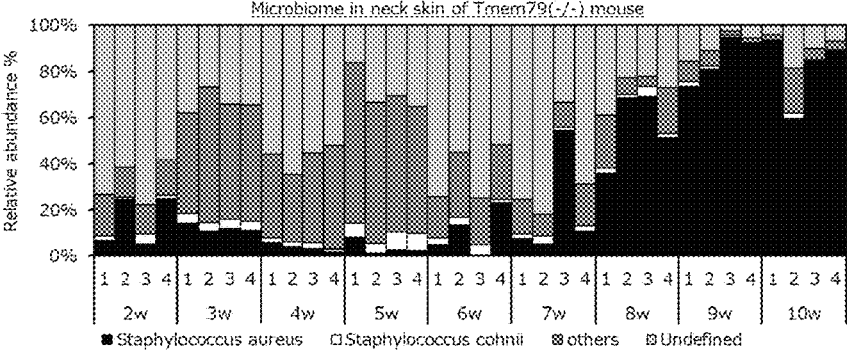

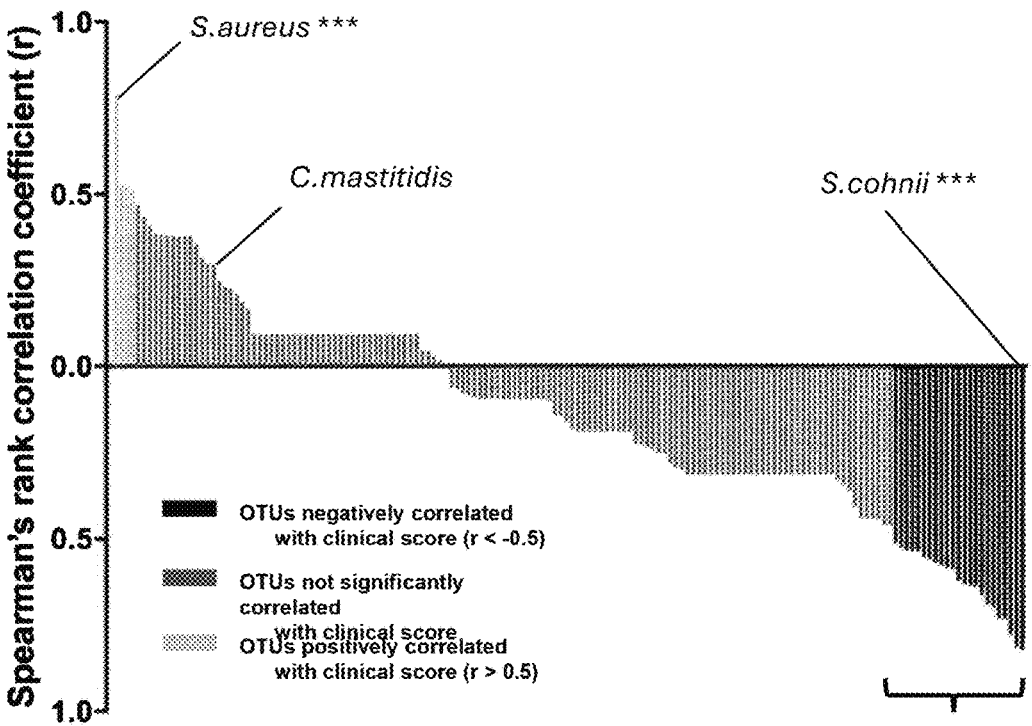

| OTU annotation | correlation coefficient | p-value |
|---|---|---|
| Bacteroides sp. SA-11 | -0.5126 | 0.0549 |
| Lactobacillus reuteri | -0.5272 | 0.0455 |
| Methylobacterium sp. RD4.1 | -0.5327 | 0.0431 |
| Methylobacterium sp. SKJH-1 | -0.5370 | 0.0407 |
| Mesorhizobium alhagi | -0.5388 | 0.0404 |
| Sphingomonas sp. MK355 | -0.5542 | 0.0571 |
| Sphingomonas sp. AC83 | -0.5589 | 0.0143 |
| Clostridium sp. Clone-16 | -0.5699 | 0.0242 |
| Pantoea sp. Ina5 | -0.5783 | 0.0262 |
| Weissella cibaria | -0.5848 | 0.0245 |
| Bradyrhizobium sp. STM 3843 | -0.5887 | 0.0249 |
| Lactococcus lactis | -0.6216 | 0.0159 |
| Afipia genosp.1 | -0.6324 | 0.0137 |
| Lactobacillus johnsonii | -0.6361 | 0.0127 |
| Methylobacterium populi | -0.6383 | 0.0122 |
| Staphylococcus arlettae | -0.6623 | 0.0066 |
| Sediminibacterium sp. IV-37 | -0.6888 | 0.0057 |
| Bradyrhizobium sp. Aust13C | -0.7002 | 0.0047 |
| Pelomonas saccharophila | -0.7319 | 0.0027 |
| Bradyrhizobium sp. Shinshu-th2 | -0.7345 | 0.0026 |
| Methylobacterium sp. BF15 | -0.7804 | 0.0010 |
| Bradyrhizobium sp. BTAi1 | -0.8139 | 0.0004 |
| Staphylococcus cohnii | -0.8237 | 0.0003 |

Fig22
A
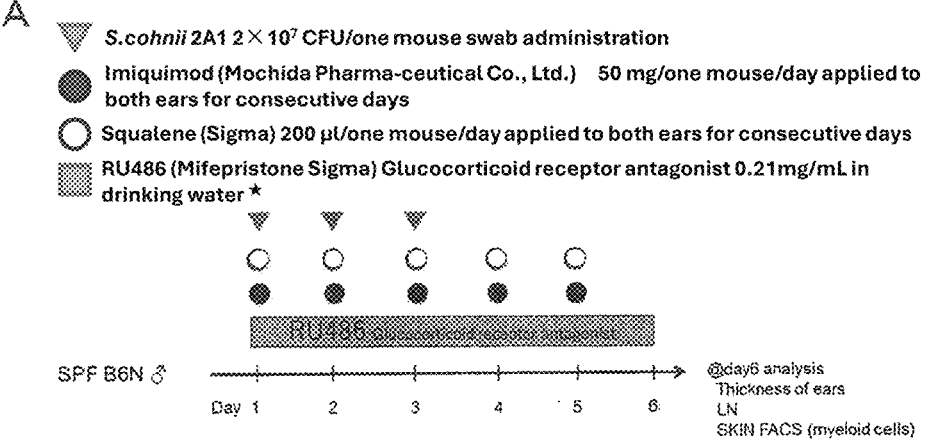
▽ *S.cohnii* 2A1 2 × 10$^7$ CFU/one mouse swab administration
⬤ Imiquimod (Mochida Pharma-ceutical Co., Ltd.)   50 mg/one mouse/day applied to both ears for consecutive days
◯ Squalene (Sigma) 200 μl/one mouse/day applied to both ears for consecutive days
▨ RU486 (Mifepristone Sigma) Glucocorticoid receptor antagonist 0.21mg/mL in drinking water ★
B    Ear thickness     C    dLN
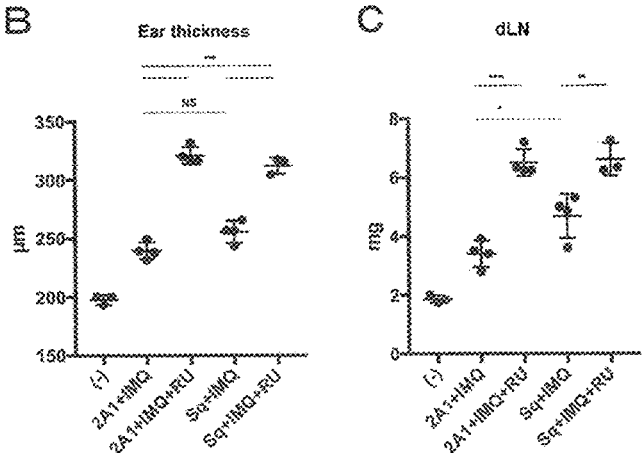

[Fig. 23A]
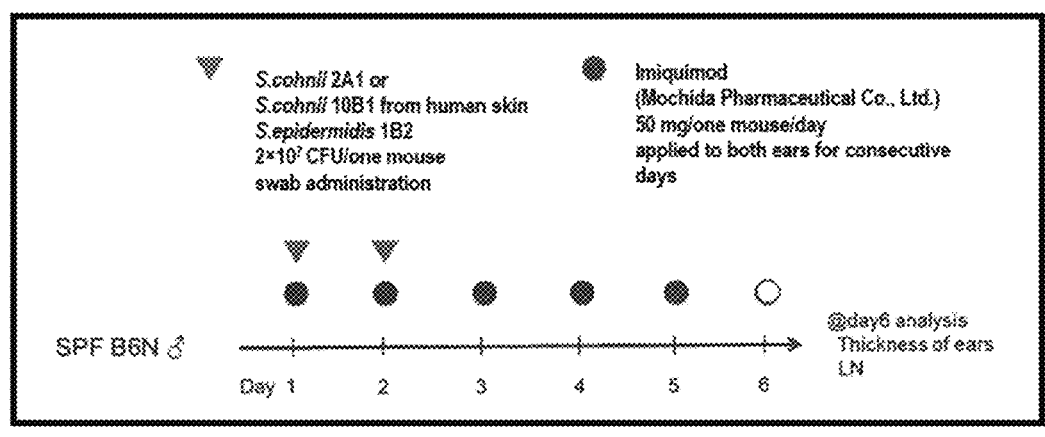
Ear thickness                              dLN
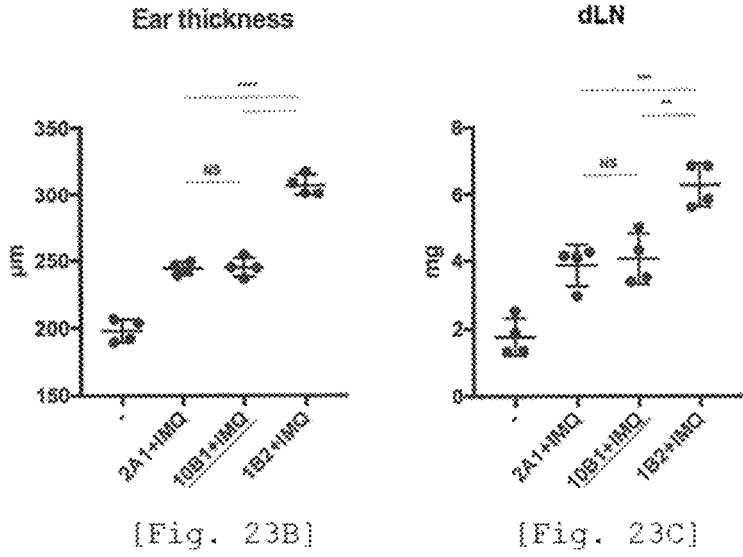
[Fig. 23B]                    [Fig. 23C]

Fig24
A
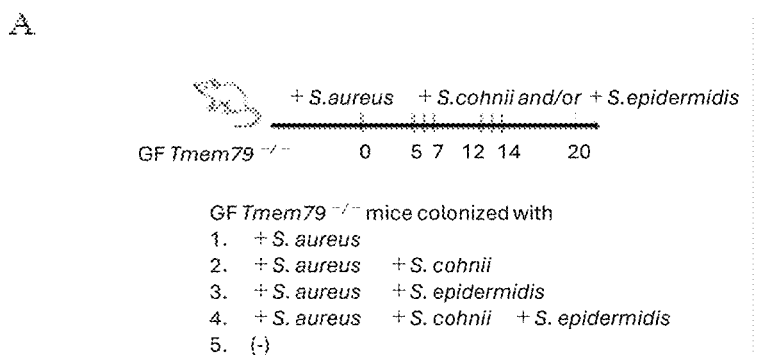
B
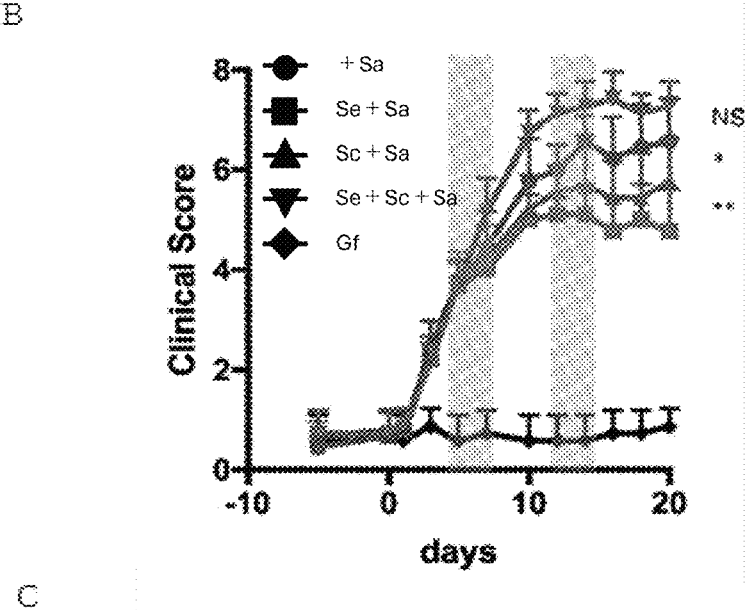
C
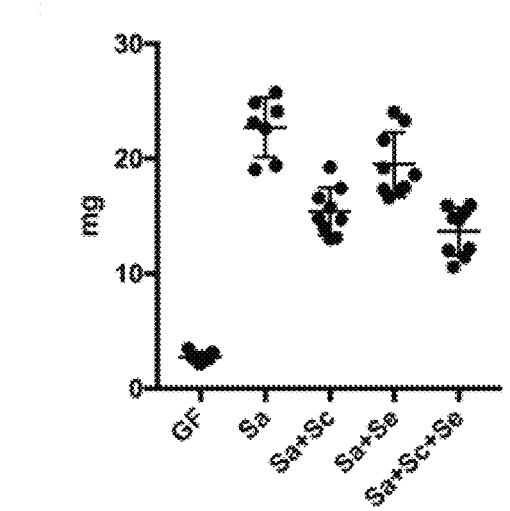

[Fig. 27]

[Fig. 29]
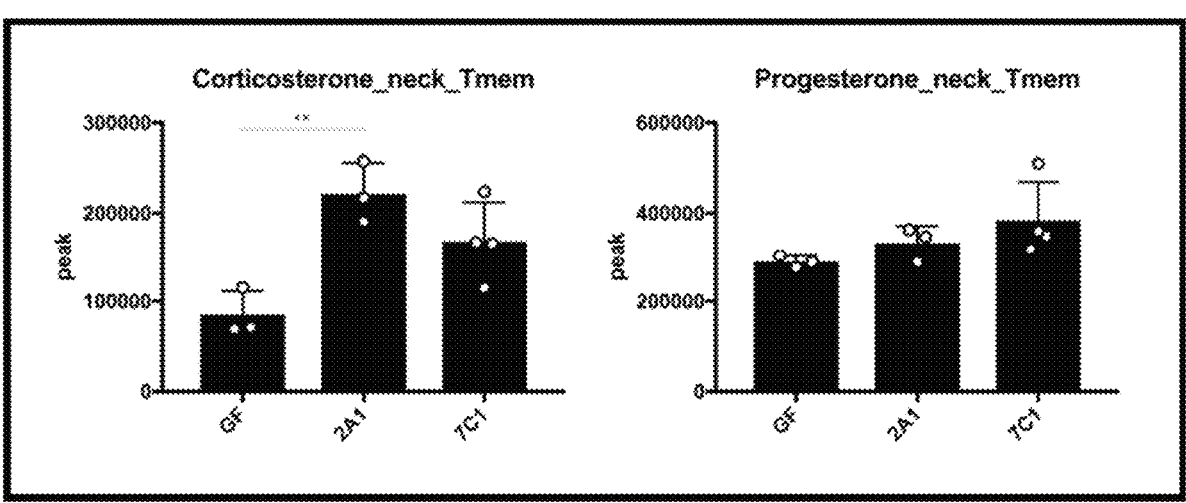

SEQUENCE LISTING

```
<160> NUMBER OF SEQ ID NOS: 11

<210> SEQ ID NO 1
<211> LENGTH: 1416
<212> TYPE: DNA
<213> ORGANISM: Staphylococcus cohnii

<400> SEQUENCE: 1
```

```
tgcaagtcga gcgaacagat aaggagcttg ctcctttgac gttagcggcg gacgggtgag     60
taacacgtgg gtaacctacc tataagactg gaataactcc gggaaaccgg ggctaatgcc    120
ggataacatt tagaaccgca tggttctaaa gtgaaagatg gttttggcta tcacttatag    180
atggacccgc gccgtattag ctagttggta aggtaacggc ttaccaaggc aacgatacgt    240
agccgacctg agagggtgat cggccacact ggaactgaga cacggtccag actcctacgg    300
gaggcagcag tagggaatct tccgcaatgg gcgaaagcct gacggagcaa cgccgcgtga    360
gtgatgaagg tcttcggatc gtaaaactct gttattaggg aagaacaaat gtgtaagtaa    420
ctgtgcacgt cttgacggta cctaatcaga aagccacggc taactacgtg ccagcagccg    480
cggtaatacg taggtggcaa gcgttatccg gaattattgg gcgtaaagcg cgcgtaggcg    540
gtttcttaag tctgatgtga aagcccacgg ctcaaccgtg gagggtcatt ggaaactggg    600
aaacttgagt gcagaagagg aaagtggaat tccatgtgta gcggtgaaat gcgcagagat    660
atggaggaac accagtggcg aaggcgactt tctggtctgt aactgacgct gatgtgcgaa    720
agcgtgggga tcaaacagga ttagataccc tggtagtcca cgccgtaaac gatgagtgct    780
aagtgttagg gggtttccgc cccttagtgc tgcagctaac gcattaagca ctccgcctgg    840
ggagtacgac cgcaaggttg aaactcaaag gaattgacgg ggacccgcac aagcggtgga    900
gcatgtggtt taattcgaag caacgcgaag aaccttacca atcttgaca tcctttgaca    960 actctagaga tagagccttc cccttcgggg acaaagtga caggtggtgc atggttgtcg   1020
tcagctcgtg tcgtgagatg ttgggttaag tcccgcaacg agcgcaaccc ttaagcttag   1080
ttgccagcat taagttgggc actctaagtt gactgccggt gacaaaccgg aggaaggtgg   1140
ggatgacgtc aaatcatcat gccccttatg atttgggcta cacacgtgct acaatggaca   1200
atacaaaggg cagctaaacc gcgaggtcat gcaaatccca taaagttgtt ctcagttcgg   1260
attgtagtct gcaactcgac tacatgaagc tggaatcgct agtaatcgta gatcagcatg   1320
ctacggtgaa tacgttcccg ggtcttgtac acaccgcccg tcacaccacg agagtttgta   1380
acacccgaag ccggtggagt aaccatttat ggagct                            1416
```

<210> SEQ ID NO 2
<211> LENGTH: 1410
<212> TYPE: DNA
<213> ORGANISM: Staphylococcus cohnii

<400> SEQUENCE: 2

```
gtcgagcgaa cagataagga gcttgctcct ttgacgttag cggcggacgg gtgagtaaca     60
cgtgggtaac ctacctataa gactggaata actccgggaa accggggcta atgccggata    120
atatttagaa ccgcatggtt ctaaagtgaa agatggtttt gctatcactt atagatggac    180
ccgcgccgta ttagctagtt ggtggggtaa tggcttacca aggcaacgat acgtagccga    240
cctgagaggg tgatcggcca cactggaact gagacacggt ccagactcct acgggaggca    300
gcagtaggga atcttccgca tgggcgaaa gcctgacgga gcaacgccgc gtgagtgatg    360
aaggtcttcg gatcgtaaaa ctctgttatt agggaagaac aaatgtgtaa gtaactgtgc    420
acgtcttgac ggtacctaat cagaaagcca cggctaacta cgtgccagca gccgcggtaa    480
tacgtaggtg gcaagcgtta tccggaatta ttgggcgtaa agcgcgcgta ggcggtttct    540
taagtctgat gtgaaagccc acggctcaac cgtggagggt cattggaaac tgggaaactt    600
gagtgcagaa gaggaaagtg gaattccatg tgtagcggtg aaatgcgcag agatatggag    660
```

-continued

```
gaacaccagt ggcgaaggcg actttctggt ctgtaactga cgctgatgtg cgaaagcgtg     720
gggatcaaac aggattagat accctggtag tccacgccgt aaacgatgag tgctaagtgt     780
taggggtttt ccgcccctta gtgctgcagc taacgcatta agcactccgc ctggggagta     840
cgaccgcaag gttgaaactc aaaggaattg acgggaccc gcacaagcgg tggagcatgt     900
ggtttaattc gaagcaacgc gaagaacctt accaaatctt gacatccttt gacaactcta     960
gagatagagt cttcccttc gggggacaaa gtgacaggtg gtgcatggtt gtcgtcagct    1020
cgtgtcgtga gatgttgggt taagtcccgc aacgagcgca acccttaagc ttagttgcca    1080
gcattaagtt gggcactcta agttgactgc cggtgacaaa ccggaggaag gtggggatga    1140
cgtcaaatca tcatgcccct tatgatttgg gctacacacg tgctacaatg gacaatacaa    1200
agggcagcta aaccgcgagg tcatgcaaat cccataaagt tgttctcagt tcggattgta    1260
gtctgcaact cgactacatg aagctggaat cgctagtaat cgtagatcag catgctacgg    1320
tgaatacgtt cccgggtctt gtacacaccg cccgtcacac cacgagagtc tgtaacaccc    1380
gaagccggtg gagtaaccat ttatggagct                                     1410

<210> SEQ ID NO 3
<211> LENGTH: 1425
<212> TYPE: DNA
<213> ORGANISM: Staphylococcus cohnii

<400> SEQUENCE: 3
tgcaagtcga gcgaacagat aaggagcttg ctcctttgac gttagcggcg gacgggtgag      60
taacacgtgg gtaacctacc tataagactg gaataactcc gggaaaccgg ggctaatgcc     120
ggataacatt tagaaccgca tggttctaaa gtgaaagatg gttttgctat cacttataga     180
tggacccgcg ccgtattagc tagttggtaa ggtaacggct taccaaggca acgatacgta     240
gccgacctga gagggtgatc ggccacactg gaactgagac acggtccaga ctcctacggg     300
aggcagcagt agggaatctt ccgcaatggg cgaaagcctg acgagcaac gccgcgtgag     360 tgatgaaggt cttcggatcg taaaactctg ttattaggga agaacaaatg tgtaagtaac     420
tgtgcacgtc ttgacggtac ctaatcagaa agccacggct aactacgtgc cagcagccgc     480
ggtaatacgt aggtggcaag cgttatccgg aattattggg cgtaaagcgc gcgtaggcgg     540
tttcttaagt ctgatgtgaa agcccacggc tcaaccgtgg agggtcattg aaactggga     600 aacttgagtg cagaagagga aagtggaatt ccatgtgtag cggtgaaatg cgcagagata     660
tggaggaaca ccagtggcga aggcgacttt ctggtctgta actgacgctg atgtgcgaaa     720
gcgtggggat caaacaggat tagataccct ggtagtccac gccgtaaacg atgagtgcta     780
agtgttaggg ggtttccgcc ccttagtgct gcagctaacg cattaagcac tccgcctggg     840
gagtacgacc gcaaggttga aactcaaagg aattgacggg acccgcaca agcggtggag     900 catgtggttt aattcgaagc aacgcgaaga accttaccaa atcttgacat cctttgacaa     960
ctctagagat agagccttcc ccttcggggg acaaagtgac aggtggtgca tggttgtcgt    1020
cagctcgtgt cgtgagatgt gggttaagt cccgcaacga gcgcaaccct taagcttagt    1080
tgccagcatt aagttgggca ctctaagttg actgccggtg acaaaccgga ggaaggtggg    1140
gatgacgtca atcatcatg cccccttatga tttgggctac acacgtgcta caatggacaa    1200
tacaaagggc agctaaaccg cgaggtcatg caaatcccat aaagttgttc tcagttcgga    1260
ttgtagtctg caactcgact acatgaagct ggaatcgcta gtaatcgtag atcagcatgc    1320
tacggtgaat acgttcccgg gtcttgtaca caccgcccgt cacaccacga gagtttgtaa    1380
```

```
cacccgaagc cggtggagta accatttatg gagctagccg tcgaa                    1425

<210> SEQ ID NO 4
<211> LENGTH: 1425
<212> TYPE: DNA
<213> ORGANISM: Staphylococcus cohnii

<400> SEQUENCE: 4
tgcaagtcga gcgaacagat aaggagcttg ctcctttgac gttagcggcg gacgggtgag     60
taacacgtgg gtaacctacc tataagactg gaataactcc gggaaaccgg ggctaatgcc    120
ggataacatt tagaaccgca tggttctaaa gtgaaagatg gttttgctat cacttataga    180
tggacccgcg ccgtattagc tagttggtaa ggtaacggct taccaaggca acgatacgta    240
gccgacctga gagggtgatc ggccacactg gaactgagac acggtccaga ctcctacggg    300
aggcagcagt agggaatctt ccgcaatggg cgaaagcctg acggagcaac gccgcgtgag    360
tgatgaaggt cttcggatcg taaaactctg ttattaggga agaacaaatg tgtaagtaac    420
tgtgcacgtc ttgacggtac ctaatcagaa agccacggct aactacgtgc cagcagccgc    480
ggtaatacgt aggtggcaag cgttatccgg aattattggg cgtaaagcgc gcgtaggcgg    540
tttcttaagt ctgatgtgaa agcccacggc tcaaccgtgg agggtcattg gaaactggga    600
aacttgagtg cagaagagga aagtggaatt ccatgtgtag cggtgaaatg cgcagagata    660
tggaggaaca ccagtggcga aggcgacttt ctggtctgta actgacgctg atgtgcgaaa    720
gcgtggggat caaacaggat tagataccct ggtagtccac gccgtaaacg atgagtgcta    780
agtgttaggg ggtttccgcc ccttagtgct gcagctaacg cattaagcac tccgcctggg    840
gagtacgacc gcaaggttga aactcaaagg aattgacggg gacccgcaca agcggtggag    900
catgtggttt aattcgaagc aacgcgaaga accttaccaa atcttgacat cctttgacaa    960
ctctagagat agagccttcc ccttcggggg acaaagtgac aggtggtgca tggttgtcgt   1020
cagctcgtgt cgtgagatgt tgggttaagt cccgcaacga gcgcaaccct taagcttagt   1080
tgccagcatt aagttgggca ctctaagttg actgccggtg acaaaccgga ggaaggtggg   1140
gatgacgtca aatcatcatg ccccttatga tttgggctac acacgtgcta caatggacaa   1200
tacaaagggc agctaaaccg cgaggtcatg caaatcccat aaagttgttc tcagttcgga   1260
ttgtagtctg caactcgact acatgaagct ggaatcgcta gtaatcgtag atcagcatgc   1320
tacggtgaat acgttcccgg gtcttgtaca caccgcccgt cacaccacga gagtttgtaa   1380
cacccgaagc cggtggagta accatttatg gagctagccg tcgaa                   1425

<210> SEQ ID NO 5
<211> LENGTH: 1416
<212> TYPE: DNA
<213> ORGANISM: Staphylococcus cohnii

<400> SEQUENCE: 5
tgcaagtcga gcgaacagat aaggagcttg ctcctttgac gttagcggcg gacgggtgag     60
taacacgtgg gtaacctacc tataagactg gaataactcc gggaaaccgg ggctaatgcc    120
ggataacatt tagaaccgca tggttctaaa gtgaaagatg gttttgctat cacttataga    180
tggacccgcg ccgtattagc tagttggtaa ggtaacggct taccaaggca acgatacgta    240
gccgacctga gagggtgatc ggccacactg gaactgagac acggtccaga ctcctacggg    300
aggcagcagt agggaatctt ccgcaatggg cgaaagcctg acggagcaac gccgcgtgag    360
```

-continued

```
tgatgaaggt cttcggatcg taaaactctg ttattaggga agaacaaatg tgtaagtaac      420
tatgcacgtc ttgacggtac ctaatcagaa agccacggct aactacgtgc cagcagccgc      480
ggtaatacgt aggtggcaag cgttatccgg aattattggg cgtaaagcgc gcgtaggcgg      540
tttcttaagt ctgatgtgaa agcccacggc tcaaccgtgg agggtcattg gaaactggga      600
aacttgagtg cagaagagga aagtggaatt ccatgtgtag cggtgaaatg cgcagagata      660
tggaggaaca ccagtggcga aggcgacttt ctggtctgta actgacgctg atgtgcgaaa      720
gcgtggggat caaacaggat tagataccct ggtagtccac gccgtaaacg atgagtgcta      780
agtgttaggg ggtttccgcc ccttagtgct gcagctaacg cattaagcac tccgcctggg      840
gagtacgacc gcaaggttga aactcaaagg aattgacggg gacccgcaca gcggtggag       900 catgtggttt aattcgaagc aacgcgaaga accttaccaa atcttgacat cctttgacaa      960
ctctagagat agagccttcc ccttcggggg acaaagtgac aggtggtgca tggttgtcgt     1020
cagctcgtgt cgtgagatgt tgggttaagt cccgcaacga gcgcaaccct taaacttagt     1080
tgccagcatt tagttgggca ctctaagttg actgccggtg acaaaccgga ggaaggtggg     1140
gatgacgtca aatcatcatg ccccttatga tttgggctac acacgtgcta caatggacaa     1200
tacaaagggc agctaaaccg cgaggtcatg caaatcccat aaagttgttc tcagttcgga     1260
ttgtagtctg caactcgact acatgaagct ggaatcgcta gtaatcgtag atcagcatgc     1320
tacggtgaat acgttcccgg gtcttgtaca caccgcccgt cacaccacga gagtttgtaa     1380
cacccgaagc cggtggagta accatttatg gagcta                                1416
```

<210> SEQ ID NO 6
<211> LENGTH: 1407
<212> TYPE: DNA
<213> ORGANISM: Staphylococcus epidermidis

<400> SEQUENCE: 6

```
tgcaagtcga gcgaacagac gaggagcttg ctcctctgac gttagcggcg gacgggtgag       60
taacacgtgg ataacctacc tataagactg ggataacttc gggaaaccgg agctaatacc      120
ggataatata ttgaaccgca tggttcaata gtgaaagacg gttttgctgt cacttataga      180
tggatccgcg ccgcattagc tagttggtaa ggtaacggct taccaaggca acgatgcgta      240
gccgacctga gagggtgatc ggccacactg gaactgagac acggtccaga ctcctacggg      300
aggcagcagt agggaatctt ccgcaatggg cgaaagcctg acggagcaac gccgcgtgag      360
tgatgaaggt cttcggatcg taaaactctg ttattaggga agaacaaatg tgtaagtaac      420
tatgcacgtc ttgacggtac ctaatcagaa agccacggct aactacgtgc cagcagccgc      480
ggtaatacgt aggtggcaag cgttatccgg aattattggg cgtaaagcgc gcgtaggcgg      540
ttttttaagt ctgatgtgaa agcccacggc tcaaccgtgg agggtcattg gaaactggaa      600
aacttgagtg cagaagagga aagtggaatt ccatgtgtag cggtgaaatg cgcagagata      660
tggaggaaca ccagtggcga aggcgacttt ctggtctgta actgacgctg atgtgcgaaa      720
gcgtggggat caaacaggat tagataccct ggtagtccac gccgtaaacg atgagtgcta      780
agtgttaggg ggtttccgcc ccttagtgct gcagctaacg cattaagcac tccgcctggg      840
gagtacgacc gcaaggttga aactcaaagg aattgacggg gacccgcaca gcggtggag       900 catgtggttt aattcgaagc aacgcgaaga accttaccaa atcttgacat cctctgaccc      960
ctctagagat agagttttcc ccttcggggg acagagtgac aggtggtgca tggttgtcgt     1020
cagctcgtgt cgtgagatgt tgggttaagt cccgcaacga gcgcaaccct taagcttagt     1080
```

-continued

```
tgccatcatt aagttgggca ctctaagttg actgccggtg acaaaccgga ggaaggtggg      1140
gatgacgtca aatcatcatg ccccttatga tttgggctac acacgtgcta caatggacaa      1200
tacaaagggc agcgaaaccg cgaggtcaag caaatcccat aaagttgttc tcagttcgga      1260
ttgtagtctg caactcgact atatgaagct ggaatcgcta gtaatcgtag atcagcatgc      1320
tacggtgaat acgttcccgg gtcttgtaca caccgcccgt cacaccacga gagtttgtaa      1380
cacccgaagc cggtggagta accattt                                          1407
```

```
<210> SEQ ID NO 7
<211> LENGTH: 1407
<212> TYPE: DNA
<213> ORGANISM: Staphylococcus lentus

<400> SEQUENCE: 7
tgcaagtcga gcgaacagat gagaagcttg cttctctgat gttagcggcg gacgggtgag       60
taacacgtgg gtaacctacc tataagactg ggataactcc gggaaaccgg ggctaatacc      120
ggataatata ttgaaccgca tggttcaatg ttgaaagacg gtttcggctg tcacttatag      180
atggacccgc gccgtattag ctagttggta aggtaacggc ttaccaaggc aacgatacgt      240
agccgacctg agagggtgat cggccacact ggaactgaga cacggtccag actcctacgg      300
gaggcagcag tagggaatct tccgcaatgg gcgaaagcct gacggagcaa cgccgcgtga      360
gtgatgaagg tcttaggatc gtaaaactct gttgttaggg aagaacaaat ttgttagtaa      420
ctgaacaagt cttgacggta cctaaccaga aagccacggc taactacgtg ccagcagccg      480
cggtaatacg taggtggcaa gcgttatccg gaattattgg gcgtaaagcg cgcgtaggcg      540
gtttcttaag tctgatgtga aagcccacgg ctcaaccgtg gagggtcatt ggaaactggg      600
gaacttgagt gcagaagagg agagtggaat tccatgtgta gcggtgaaat gcgcagagat      660
atggaggaac accagtggcg aaggcggctc tctggtctgt aactgacgct gatgtgcgaa      720
agcgtgggga tcaaacagga ttagataccc tggtagtcca cgccgtaaac gatgagtgct      780
aagtgttagg gggtttccgc cccttagtgc tgcagctaac gcattaagca ctccgcctgg      840
ggagtacgac cgcaaggttg aaactcaaag gaattgacgg ggacccgcac aagcggtgga      900
gcatgtggtt taattcgaag caacgcgaag aaccttacca atcttgaca tcctttgatc      960 gctctagaga tagagttttc cccttcgggg acaaagtga caggtggtgc atggttgtcg     1020
tcagctcgtg tcgtgagatg ttgggttaag tcccgcaacg agcgcaaccc ttaagcttag     1080
ttgccatcat taagttgggc actctaggtt gactgccggt gacaaaccgg aggaaggtgg     1140
ggatgacgtc aaatcatcat gccccttatg atttgggcta cacacgtgct acaatggata     1200
atacaaaggg cagcgaaccc gcgaggtcaa gcaaatccca taaaattatt ctcagttcgg     1260
attgtagtct gcaactcgac tacatgaagc tggaatcgct agtaatcgta gatcagcatg     1320
ctacggtgaa tacgttcccg gtcttgtac acaccgcccg tcacaccacg agagtttgta     1380
acacccgaag ccggtggagt aacctttt                                        1407
```

```
<210> SEQ ID NO 8
<211> LENGTH: 1399
<212> TYPE: DNA
<213> ORGANISM: Staphylococcus aureus

<400> SEQUENCE: 8
agtcgagcga acggacgaga agcttgcttc tctgatgtta gcggcggacg ggtgagtaac       60
```

-continued

```
acgtggataa cctacctata agactgggat aacttcggga aaccggagct aataccggat      120
aatattttga accgcatggt tcaaaagtga aagacggtct tgctgtcact tatagatgga      180
tccgcgctgc attagctagt tggtaaggta acggcttacc aaggcaacga tgcatagccg      240
acctgagagg gtgatcggcc acactggaac tgagacacgg tccagactcc tacgggaggc      300
agcagtaggg aatcttccgc aatgggcgaa agcctgacgg agcaacgccg cgtgagtgat      360
gaaggtcttc ggatcgtaaa actctgttat tagggaagaa catatgtgta agtaactgtg      420
cacatcttga cggtacctaa tcagaaagcc acggctaact acgtgccagc agccgcggta      480
atacgtaggt ggcaagcgtt atccggaatt attgggcgta aagcgcgcgt aggcggtttt      540
ttaagtctga tgtgaaagcc cacggctcaa ccgtggaggg tcattggaaa ctggaaaact      600
tgagtgcaga agaggaaagt ggaattccat gtgtagcggt gaaatgcgca gagatatgga      660
ggaacaccag tggcgaaggc gactttctgg tctgtaactg acgctgatgt gcgaaagcgt      720
ggggatcaaa caggattaga taccctggta gtccacgccg taaacgatga gtgctaagtg      780 ttaggggggtt tccgcccctt agtgctgcag ctaacgcatt aagcactccg cctggggagt      840
acgaccgcaa ggttgaaact caaaggaatt gacggggacc cgcacaagcg gtggagcatg      900
tggtttaatt cgaagcaacg cgaagaacct taccaaatct tgacatcctt tgacaactct      960
agagatagag ctttcccctt cgggggacaa agtgacaggt ggtgcatggt tgtcgtcagc     1020
tcgtgtcgtg agatgttggg ttaagtcccg caacgagcgc aacccttaag cttagttgcc     1080
atcattaagt tgggcactct aagttgactg ccggtgacaa accggaggaa ggtggggatg     1140
acgtcaaatc atcatgcccc ttatgatttg ggctacacac gtgctacaat ggacaataca     1200
aagggcagcg aaaccgcgag gtcaagcaaa tcccataaag ttgttctcag ttcggattgt     1260
agtctgcaac tcgactacat gaagctggaa tcgctagtaa tcgtagatca gcatgctacg     1320
gtgaatacgt tcccgggtct tgtacacacc gcccgtcaca ccacgagagt ttgtaacacc     1380
cgaagccggt ggagtaacc                                                  1399
```

```
<210> SEQ ID NO 9
<211> LENGTH: 1385
<212> TYPE: DNA
<213> ORGANISM: Corynebacterium mastitidis

<400> SEQUENCE: 9
tgcaagtcga acggaaaggc ctcagcttgc tggggggtact cgagtggcga acgggtgagt       60
aacacgtggg tgatctgccc tcaacttcgg gataagcttg ggaaactggg tctaataccg      120
gataggacca tggtttagtg ttcatggtgg aaagctttat gtggttgggg atgagctcgc      180
ggcctatcag cttgttggtg gggtaatggc ctaccaaggc ggcgacgggt agccggcctg      240
agagggtgta cggccacatt gggactgaga tacggcccag actcctacgg gaggcagcag      300 tgggggaatat tgcacaatgg gcgcaagcct gatgcagcga cgccgcgtgg gggatgaagg      360
ccttcgggtt gtaaactcct ttcgctaccg acgaagccct tgggggtgac ggtaggtgga      420
gaagaagcac cggctaacta cgtgccagca gccgcggtaa tacgtagggt gcgagcgttg      480
tccggattta ctgggcgtaa agagctcgta ggtggtttgt cgcgtcgtct gtgaaattcc      540
ggggcttaac tccgggcgtg caggcgatac gggcataact tgagtgctgt aggggtaact      600
ggaattcctg tgtagcggt ggaatgcgca gatatcagga ggaacaccga tggcgaaggc      660
aggttactgg gcagttactg acgctgagga gcgaaagcat gggtagcgaa caggattaga      720
taccctggta gtccatgctg taaacggtgg gcgctaggtg tgagcctctt ccacgggggtt      780
```

-continued

```
tgtgccgtag ctaacgcatt aagcgccccg cctggggagt acggccgcaa ggctaaaact    840
caaaggaatt gacgggggcc cgcacaagcg gcggagcatg tggattaatt cgatgcaacg    900
cgaagaacct tacctgggct tgacatacac cagatcggcg cagagatgcg ttttcccttt    960
gtggttggtg tacaggtggt gcatggttgt cgtcagctcg tgtcgtgaga tgttgggtta   1020
agtcccgcaa cgagcgcaac ccttgtctta tgttgccagc acgtggtggt ggggactcat   1080
gagagactgc cggggttaac tcggaggaag gtggggatga cgtcaaatca tcatgcccct   1140
tatgtccagg gcttcacaca tgctacaatg gtcggtacag taggttgcga taccgtgagg   1200
tggagctaat ccttgtaaag tcggccttag ttcggattgg ggtctgcaac tcgacccca   1260 gaagtcggag tcgctagtaa tcgcagatca gcaacgctgc ggtgaatacg ttcccgggcc   1320
ttgtacacac cgcccgtcac gtcatgaaag ttggtaacac ccgaaaacca tggcctaacc   1380
cttgt                                                              1385

<210> SEQ ID NO 10
<211> LENGTH: 21
<212> TYPE: DNA
<213> ORGANISM: Artificial sequence
<220> FEATURE:
<223> OTHER INFORMATION: forward primer for GADPH

<400> SEQUENCE: 10
cctcgtcccg tagacaaaat g                                               21

<210> SEQ ID NO 11
<211> LENGTH: 20
<212> TYPE: DNA
<213> ORGANISM: Artificial sequence
<220> FEATURE:
<223> OTHER INFORMATION: reverse primer for GADPH

<400> SEQUENCE: 11
tctccacttt gccactgcaa                                                 20
```

PHARMACEUTICAL COMPOSITION FOR PREVENTION, AMELIORATION, OR TREATMENT OF SKIN DISEASE

TECHNICAL FIELD

The present invention relates to a pharmaceutical composition for prevention, amelioration, or treatment of skin disease, and the like.

BACKGROUND ART

In humans, animals, and the like, it is known that certain groups of microorganisms exist in a part that comes into contact with the outside, such as the skin or the mucous membrane, and such a bacterial group is referred to as normal bacterial flora. The species and proportion of the bacteria contained in normal bacterial flora vary depending on the biological species, the individual, or the body part. Further, such a normal bacterial flora plays an extremely important role in the homeostasis and immune response of the host, and it has become clear in recent years that changes in the normal bacterial flora in the gastrointestinal tract, skin, or the like are associated with various inflammations and diseases.

Atopic dermatitis (AD) is a skin disease associated with repeatedly occurring intense itching and rash, and the mechanism of the onset is not clearly understood, and it is considered that multiple factors are related. The skin disease associated with abnormalities on the skin, such as atopic dermatitis causes not only physical pain such as itching but also deterioration of physical appearance, resulting in a reduction in the quality of life (QOL) of a patient, and thus, measures that can ameliorate the skin disease have been widely demanded.

In this regard, it has been reported that a patient with atopic dermatitis has "disturbance of normal bacterial flora" (dysbiosis) in the skin. It is known that the proportion of *Staphylococcus aureus* is higher in the normal bacterial flora in the skin of a patient with atopic dermatitis than that in the normal bacterial flora in the skin of a healthy person, and it has been reported that the proliferation of the bacteria is associated with the state of disease. For example, it has been reported that in the skin of a pathological mouse of atopic dermatitis in the settled state of disease, other bacteria belonging to the genus *Staphylococcus* (hereinafter, may be abbreviated as "S." as the genus name) become dominant in the normal bacterial flora, and further, some of these bacteria produce antimicrobial peptides against *S. aureus* (Non Patent Literature 1).

In addition, in Non Patent Literature 2, it has been reported that the colonization of *Staphylococcus* in the skin in the early postnatal period is associated with a lower risk of developing atopic dermatitis, and it is known that *Staphylococcus cohnii* and *Staphylococcus epidermidis* are dominant in the bacterial flora in the skin of a 12-month-old non-dermatitis infant, and the *Staphylococcus epidermidis* initiates immune response of the host against pathogens. However, there are still many unclear points such as the relationship between the skin normal bacterial flora and the host, the skin disease, or the like, and the influence and mechanism of the skin normal bacterial flora on skin disease.

Tmem79 that is a transmembrane protein expressed in the outermost layer (SG1) of a granular layer in the epidermis is a protein colocalized with the trans-Golgi apparatus, and is also a protein that works in connection with the transport of proteins and lipids to the outside of the cell. It has been reported that a mouse of which the Tmem79 has been mutated forms abnormal stratum corneum in the skin and spontaneously develops dermatitis (Non Patent Literature 3). In addition, the associations between polymorphisms of Tmem79 and atopic dermatitis are known in Irish genetic polymorphism analysis (Non Patent Literature 4).

CITATION LIST

Non Patent Literature

Non Patent Literature 1: Antimicrobials from human skin commensal bacteria protect against *Staphylococcus aureus* and are deficient in atopic dermatitis (Sci. Transl. Med. 2017 Feb. 22; 9 (378))

Non Patent Literature 2: Skin microbiome before development of atopic dermatitis: Early colonization with commensal staphylococci at 2 months is associated with a lower risk of atopic dermatitis at 1 year (J. Allergy Clin. Immunol. 2017 January; 139(1): 166-172)

Non Patent Literature 3: Immunological Medicine 37(4), p. 370b, 2014

Non Patent Literature 4: Tmem79/Matt is the matted mouse gene and is a predisposing gene for atopic dermatitis in human subjects (J. Allergy Clin. Immunol. 2013 November; 132(5): 1121-9)

SUMMARY OF INVENTION

Technical Problem

An object of the present invention is to examine the influence by flora of the skin on dermatitis by analyzing the skin of a Tmem79-knockout model mouse (hereinafter, also referred to as "Tmem79$^{-/-}$ mouse" or "Tmem79-KO mouse"), to identify a bacterium having a suppressive effect on dermatitis, and to provide a pharmaceutical composition derived from such a bacterium.

Solution to Problem

The inventors have narrowed down the bacteria of a Tmem79-KO mouse, which are dominant in a situation where the immune response or inflammation of a host is suppressed in the process of initiating dermatitis, and have been revealed that the bacterium belonging to the genus *Staphylococcus* being one species of skin normal bacteria has a preventive, ameliorative, or therapeutic effect on dermatitis. Further, the inventors have found that these bacteria act on the host and enhance the glucocorticoid gene expression in the host.

That is, the present invention provides, for example, the following [1] to [80].

[1]

A pharmaceutical composition, including as active components one or more substances selected from the following (a) to (d):

(a) a bacterial cell of a bacterium sensitive to ampicillin or a constituent component of the bacterium;

(b) a culture supernatant of a bacterium sensitive to ampicillin or a purified product from the culture supernatant;

(c) an extract of a bacterium sensitive to ampicillin; and (d) a metabolite of a bacterium sensitive to ampicillin.

3

[2]

The pharmaceutical composition described in [1], in which the bacterium sensitive to ampicillin is a fusidic acid-resistant bacterium.

[3]

The pharmaceutical composition described in [1] or [2], in which the bacterium sensitive to ampicillin is a bacterium (excluding *S. aureus*) belonging to the genus *Staphylococcus*, being resistant to fusidic acid.

[4]

The pharmaceutical composition described in any one of [1] to [3], in which the bacterium sensitive to ampicillin is selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans.*

[5]

The pharmaceutical composition described in any one of [1] to [4], in which a 16S rDNA gene sequence of the bacterium sensitive to ampicillin is a sequence represented by any one of SEQ ID NOs: 1 to 7, or a sequence having at least 90% or more sequence identity to the sequence represented by any one of SEQ ID NOs: 1 to 7.

[6]

The pharmaceutical composition described in any one of [1] to [5], in which the bacterium sensitive to ampicillin is selected from one or more bacteria deposited under Accession numbers NITE BP-02848, NITE BP-02850, NITE BP-02851, NITE BP-02852, NITE BP-02853, NITE BP-02845, and NITE BP-02847.

[7]

The pharmaceutical composition described in any one of [1] to [6], in which the bacterium sensitive to ampicillin is *S. cohnii.*

[8]

The pharmaceutical composition described in [7], in which a 16S rDNA gene sequence of the *S. cohnii* is a sequence represented by any one of SEQ ID NOs: 1 to 5, or a sequence having at least 90% or more sequence identity to the sequence represented by any one of SEQ ID NOs: 1 to 5.

[9]

The pharmaceutical composition described in [7] or [8], in which the *S. cohnii* is selected from one or more bacteria deposited under Accession numbers NITE BP-02848, NITE BP-02850, NITE BP-02851, NITE BP-02852, and NITE BP-02853.

[10]

The pharmaceutical composition described in any one of [1] to [9], in which the bacterium sensitive to ampicillin is a bacterium derived from a human.

[11]

The pharmaceutical composition described in any one of [1] to [10], in which the bacterium sensitive to ampicillin is a live bacterium, a killed bacterium, or a mixture of the live bacterium and the killed bacterium.

[12]

The pharmaceutical composition described in any one of [1] to [11], in which the pharmaceutical composition is for treatment, amelioration, or prevention of skin disease.

[13]

The pharmaceutical composition described in [12], in which the skin disease is dermatitis.

4

[14]

The pharmaceutical composition described in [12], in which the skin disease is atopic dermatitis.

[15]

The pharmaceutical composition described in [12], in which the skin disease is dermatitis initiated by an IFN-α production promoter.

[16]

The pharmaceutical composition described in [12], in which the skin disease is dermatitis initiated by a preparation containing an imidazoquinoline derivative.

[17]

The pharmaceutical composition described in [12], in which the skin disease is dermatitis initiated by imiquimod.

[18]

The pharmaceutical composition described in [12], in which the skin disease is psoriasis.

[19]

The pharmaceutical composition described in [12], in which the skin disease is autoimmune skin disease.

[20]

A method for producing the pharmaceutical composition described in any one of [1] to [19].

[21]

An activator, including a bacterium sensitive to ampicillin, in which the activator is used for at least one or more applications selected from treatment of skin disease, amelioration of skin disease, prevention of skin disease, proliferation of the bacterium, and amelioration of skin condition.

[22]

The activator described in [21], in which the bacterium sensitive to ampicillin is a fusidic acid-resistant bacterium.

[23]

The activator described in [21] or [22], in which the bacterium sensitive to ampicillin is a bacterium (excluding *S. aureus*) belonging to the genus *Staphylococcus*, being a fusidic acid-resistant bacterium.

[24]

The activator described in any one of [21] to [23], in which the bacterium sensitive to ampicillin is selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans.*

[25]

The activator described in any one of [21] to [24], further including a steroid biosynthesis-related protein as an active component.

[26]

The activator described in [25], in which the steroid biosynthesis-related protein is squalene synthase.

[27]

An activator of a bacterium sensitive to ampicillin, including an anti-*S. aureus* antibody as an active component.

[28]

An inhibitor of *S. aureus*, including as active components, one or more substances selected from an anti-*S. aureus* antibody, a bacterial cell of a bacterium sensitive to ampicillin, a constituent component of the bacterium, a culture supernatant of the bacterium, a purified product from the culture supernatant, an extract of the bacterium, and a metabolite of the bacterium.

[29]

The inhibitor of *S. aureus* described in [28], in which the bacterium sensitive to ampicillin is a fusidic acid-resistant bacterium.

[30]

The inhibitor of *S. aureus* described in [28] or [29], in which the bacterium sensitive to ampicillin is a bacterium (excluding *S. aureus*) belonging to the genus *Staphylococcus*, being a fusidic acid-resistant bacterium.

[31]

The inhibitor of *S. aureus* described in any one of [28] to [30], in which the bacterium sensitive to ampicillin is selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans*.

[32]

The inhibitor of *S. aureus* described in any one of [28] to [31], in which the bacterium sensitive to ampicillin is *S. cohnii*.

[33]

The inhibitor of *S. aureus* described in any one of [28] to [32], further including an anti-*S. aureus* antibody as an active component.

[34]

A therapeutic agent for skin disease, including, as active components, one or more substances selected from a bacterial cell of a bacterium sensitive to ampicillin, a constituent component of the bacterium, a culture supernatant of the bacterium, a purified product from the culture supernatant, an extract of the bacterium, and a metabolite of the bacterium.

[35]

The therapeutic agent for skin disease described in [34], in which the bacterium sensitive to ampicillin is a fusidic acid-resistant bacterium.

[36]

The therapeutic agent for skin disease described in [34] or [35], in which the bacterium sensitive to ampicillin is a bacterium (excluding *S. aureus*) belonging to the genus *Staphylococcus*, being resistant to fusidic acid.

[37]

The therapeutic agent for skin disease described in any one of [34] to [36], in which the bacterium sensitive to ampicillin is selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans*.

[38]

The therapeutic agent for skin disease described in any one of [34] to [37], in which the bacterium sensitive to ampicillin is *S. cohnii*.

[39]

A method for suppressing proliferation of *S. aureus*, including applying one or more substances selected from an anti-*S. aureus* antibody, a bacterial cell of a bacterium sensitive to ampicillin, a constituent component of the bacterium, a culture supernatant of the bacterium, a purified product from the culture supernatant, an extract of the bacterium, and a metabolite of the bacterium.

[40]

The method for suppressing proliferation of *S. aureus* described in [39], in which the bacterium sensitive to ampicillin is a fusidic acid-resistant bacterium.

[41]

The method for suppressing proliferation of *S. aureus* described in [39] or [40], in which the bacterium sensitive to ampicillin is a bacterium (excluding *S. aureus*) belonging to the genus *Staphylococcus*, being an ampicillin-sensitive and fusidic acid-resistant bacterium.

[42]

The method for suppressing proliferation of *S. aureus* described in any one of [39] to [41], in which the bacterium sensitive to ampicillin is selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans*.

[43]

The method for suppressing proliferation of *S. aureus* described in any one of [39] to [42], in which the bacterium sensitive to ampicillin is *S. cohnii*.

[44]

A method for suppressing proliferation of *S. aureus*, including applying one or more substances selected from a bacterial cell of a bacterium of *S. cohnii*, a constituent component of the bacterium, a culture supernatant of the bacterium, a purified product from the culture supernatant, an extract of the bacterium, and a metabolite of the bacterium.

[45]

A method for enhancing transcription of a glucocorticoid-responsive gene, including using one or more substances selected from a bacterial cell of a bacterium sensitive to ampicillin, a constituent component of the bacterium, a culture supernatant of the bacterium, a purified product from the culture supernatant, an extract of the bacterium, and a metabolite of the bacterium.

[46]

The method for enhancing transcription of a glucocorticoid-responsive gene described in [45], in which the bacterium sensitive to ampicillin is a fusidic acid-resistant bacterium.

[47]

The method for enhancing transcription of a glucocorticoid-responsive gene described in [45] or [46], in which the bacterium sensitive to ampicillin is a bacterium (excluding *S. aureus*) belonging to the genus *Staphylococcus*, being sensitive to ampicillin and resistant to fusidic acid.

[48]

The method for enhancing transcription of a glucocorticoid-responsive gene described in any one of [45] to [47], in which the bacterium sensitive to ampicillin is selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans*.

[49]

The method for enhancing transcription of a glucocorticoid-responsive gene described in any one of [45] to [48], in which the bacterium sensitive to ampicillin is one or more bacteria of *S. cohnii* and *S. lentus*.

[50]

The method for enhancing transcription of a glucocorticoid-responsive gene described in any one of [45] to [49], in which the glucocorticoid-responsive gene is one or more genes selected from Fkbp5, Zbtb16, and Tsc22d3.

[51]

The method for enhancing transcription of a glucocorticoid-responsive gene described in any one of [45] to [50], in which the glucocorticoid-responsive gene is a gene encoding a steroid biosynthesis-related protein.

[52]

The method for enhancing transcription of a glucocorticoid-responsive gene described in [51], in which the steroid biosynthesis-related protein is squalene synthase.

[53]

A method for analyzing flora present on the skin of a living organism having skin disease.

[54]

The method for analyzing flora described in [53], in which the living organism having skin disease is a Tmem79$^{-/-}$ mouse.

[55]

The method for analyzing flora described in [53] or [54], in which the living organism having skin disease is a specific pathogen-free (SPF) animal.

[56]

A method for assisting selection of a treatment method for a living organism having skin disease, including the steps of:

(1) calculating a ratio of *S. aureus* to skin normal bacterial flora in a skin sample collected from a disease site of the living organism; and (2) selecting in a case where the ratio is higher than a reference value, a pharmaceutical composition containing as active components one or more substances selected from the following (a) to (d):

(a) a bacterial cell of a bacterium sensitive to ampicillin or a constituent component of the bacterium;

(b) a culture supernatant of a bacterium sensitive to ampicillin or a purified product from the culture supernatant;

(c) an extract of a bacterium sensitive to ampicillin; and (d) a metabolite of a bacterium sensitive to ampicillin.

[57]

The method for assisting selection of a treatment method described in [56], in which the bacterium sensitive to ampicillin is a fusidic acid-resistant bacterium.

[58]

The method for assisting selection of a treatment method described in [56] or [57], in which the bacterium sensitive to ampicillin is a bacterium (excluding *S. aureus*) belonging to the genus *Staphylococcus*, being resistant to fusidic acid.

[59]

The method for assisting selection of a treatment method described in any one of [56] to [58], in which the bacterium sensitive to ampicillin is selected from one or more species of *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*.

[60]

The method for assisting selection of a treatment method described in any one of [56] to [59], in which the reference value is (i) an average value of ratios of *S. aureus* to skin normal bacterial flora in skin samples of individuals having no skin disease, the individuals being living organisms of the same species as the living organism having skin disease, or (ii) a ratio of *S. aureus* to skin normal bacterial flora in a skin sample collected from a site other than a disease site of the living organism having skin disease.

[61]

A method for obtaining auxiliary information about treatment of skin disease in a living organism having skin disease, including the steps of:

(1) calculating a ratio of *S. aureus* to skin normal bacterial flora in a skin sample collected from a living organism having skin disease before treatment of the skin disease;

(2) calculating a ratio of *S. aureus* to skin normal bacterial flora in a skin sample collected from a living organism having skin disease after treatment of the skin disease; and (3) comparing the ratio calculated in step (1) with the ratio calculated in step (2).

[62]

An anti-*S. aureus* antibody and/or a steroid biosynthesis-related protein, for use in treatment of skin disease.

[63]

Use of one or more substances selected from an anti-*S. aureus* antibody and a steroid biosynthesis-related protein, for producing a medicine for treatment of skin disease.

[64]

A method for treatment of skin disease, including administering to a patient one or more substances selected from an anti-*S. aureus* antibody and a steroid biosynthesis-related protein.

[65]

A bacterial cell of a bacterium sensitive to ampicillin, a constituent component of the bacterium, a culture supernatant of the bacterium, a purified product from the culture supernatant, an extract of the bacterium, or a metabolite of the bacterium, for use in treatment of skin disease.

[66]

The bacterial cell of a bacterium sensitive to ampicillin, the constituent component of the bacterium, the culture supernatant of the bacterium, the purified product from the culture supernatant, the extract of the bacterium, or the metabolite of the bacterium described in [70], in which the bacterium is a fusidic acid-resistant bacterium.

[67]

The bacterial cell of a bacterium sensitive to ampicillin, the constituent component of the bacterium, the culture supernatant of the bacterium, the purified product from the culture supernatant, the extract of the bacterium, or the metabolite of the bacterium described in [65] or [66], in which the bacterium is a bacterium (excluding *S. aureus*) belonging to the genus *Staphylococcus*, being resistant to fusidic acid.

[68]

The bacterial cell of a bacterium sensitive to ampicillin, the constituent component of the bacterium, the culture supernatant of the bacterium, the purified product from the culture supernatant, the extract of the bacterium, or the metabolite of the bacterium described in any one of [65] to [67], in which the bacterium is selected from one or more species of *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*.

[69]

A bacterial cell of *S. cohnii*, a constituent component of the bacterium, a culture supernatant of the bacterium, a purified product from the culture supernatant, an extract of the bacterium, or a metabolite of the bacterium, for use in treatment of skin disease.

[70]

Use of one or more substances selected from a bacterial cell of a bacterium sensitive to ampicillin, a constituent component of the bacterium, a culture supernatant of the bacterium, a purified product from the culture supernatant, an extract of the bacterium, and a metabolite of the bacterium, for producing a medicine for treatment of skin disease.

[71]

The use described in [70], in which the bacterium sensitive to ampicillin is a fusidic acid-resistant bacterium.

[72]

The use described in [70] or [71], in which the bacterium sensitive to ampicillin is a bacterium (excluding *S. aureus*) belonging to the genus *Staphylococcus*, being resistant to fusidic acid.

[73]

The use described in any one of [70] to [72], in which the bacterium sensitive to ampicillin is selected from one or more species of *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*.

[74]

The use described in any one of [70] to [73], in which the bacterium is *S. cohnii*.

[75]

A method for treatment of skin disease, including administering to a patient one or more substances selected from a bacterial cell of a bacterium sensitive to ampicillin, a constituent component of the bacterium, a culture supernatant of the bacterium, a purified product from the culture supernatant, an extract of the bacterium, and a metabolite of the bacterium.

[76]

The method for treatment of skin disease described in [75], in which the bacterium sensitive to ampicillin is a fusidic acid-resistant bacterium.

[77]

The method for treatment of skin disease described in [75] or [76], in which the bacterium sensitive to ampicillin is a bacterium (excluding *S. aureus*) belonging to the genus *Staphylococcus*, being sensitive to ampicillin and resistant to fusidic acid.

[78]

The method for treatment of skin disease described in any one of [75] to [77], in which the bacterium sensitive to ampicillin is selected from one or more species of *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*.

[79]

The method for treatment of skin disease described in any one of [75] to [78], in which the bacterium is *S. cohnii*.

[80]

A bacterium strain belonging to the species *S. cohnii* specified by Accession number NITE BP-02848, NITE BP-02850, NITE BP-02851, NITE BP-02852, or NITE BP-02853.

Advantageous Effects of Invention

According to the present invention, it can be realized to control skin disease by a pharmaceutical composition derived from specific skin normal bacteria.

BRIEF DESCRIPTION OF DRAWINGS

Hereinafter, SPF WT in drawings is synonymous with SPF-WT in the present specification. Similarly, SPF Tmem79$^{-/-}$ is synonymous with SPF-Tmem79$^{-/-}$, GF Tmem79$^{-/-}$ is synonymous with GF-Tmem79$^{-/-}$, and GF WT is synonymous with GF-WT.

FIG. 2 shows results of meta-16S analysis of bacterial flora, performed by using the skins of SPF-WT mice and SPF-Tmem79$^{-/-}$ mice.

FIG. 22A is a schematic diagram showing an experimental flow. FIGS. 22B and 22C show results of verification of the effect of squalene on inflammation of the GF-WT mice applied with imiquimod cream (IMQ), on the basis of ear swelling and lymph node swelling.

FIG. 23A is a schematic diagram showing an experimental flow. FIGS. 23B and 23C show results of verification of the suppressive effect of a human-derived *S. cohnii* 10B1 strain (SEQ ID NO: 57, deposited under Accession number: NITE BP-02853) on inflammation of the SPF-WT mice applied with imiquimod cream, on the basis of the degree of ear swelling and lymph node swelling.

FIG. 24A is a schematic diagram showing an experimental flow. FIG. 24B shows results of verification using clinical scores of the *S. aureus*-dependent inflammation suppressive effect by *S. cohnii, S. epidermidis*, or in combination thereof, and FIG. 24C shows results of verification performed on the basis of the degree of cervical lymph node swelling.

Figure 25:
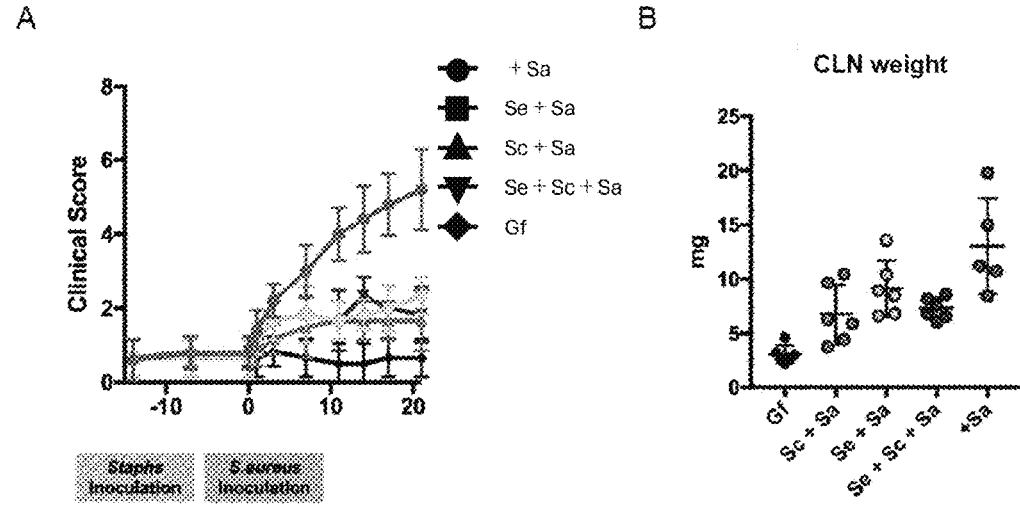

FIG. 25A shows results of verification using clinical scores of the *S. aureus*-dependent inflammation preventive effect by *S. cohnii, S. epidermidis*, or in combination thereof, and FIG. 25B shows results of verification performed on the basis of the degree of lymph node swelling.

Figure 26:
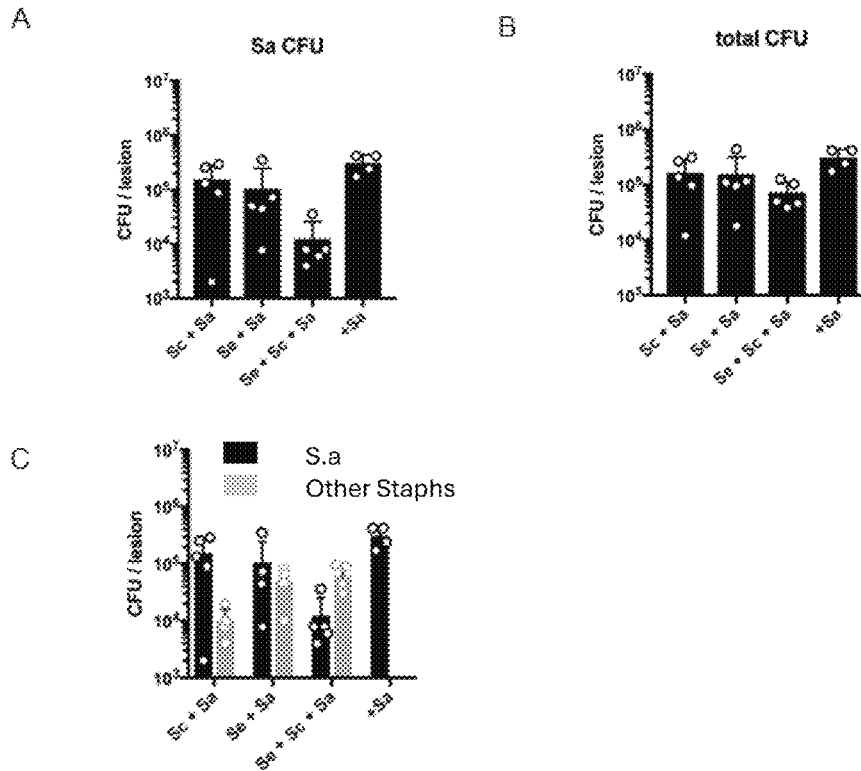

FIGS. 26A to 26C show results of observation of changes in the amount of bacteria of the GF-Tmem79-KO mouse inoculated with *S. aureus* alone, *S. aureus* and *S. cohnii, S. aureus* and *S. epidermidis*, and *S. aureus, S. cohnii*, and *S. epidermidis*, respectively.

Figure 27:
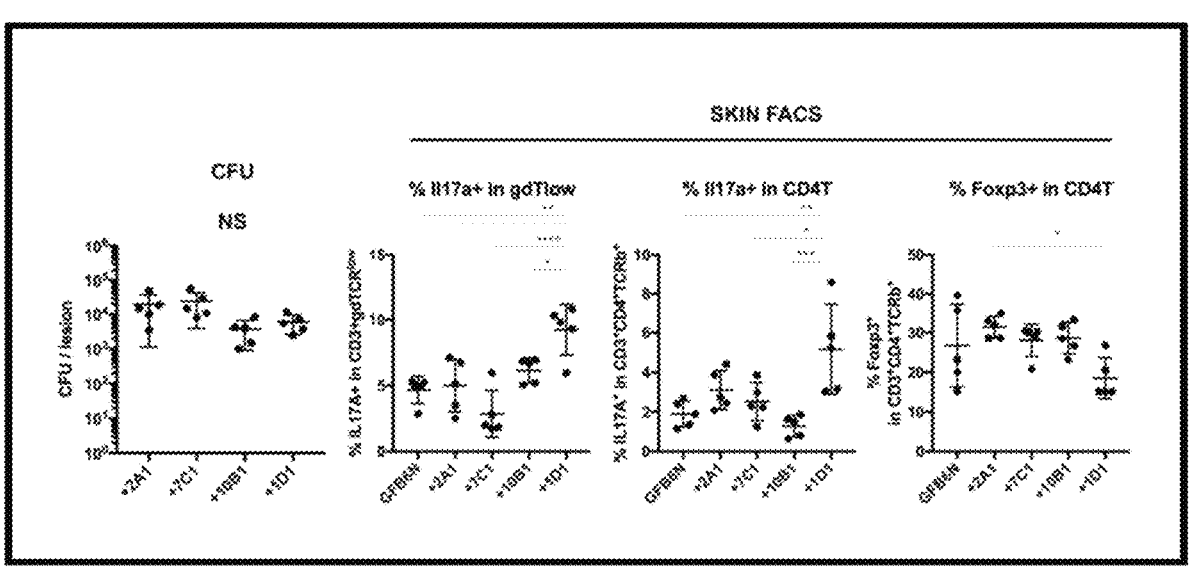

FIG. 27 shows the amounts of bacteria measured by using the skin of mouse inoculated with *S. cohnii* or *S. aureus*, and the results of FACS analysis.

Figure 28:
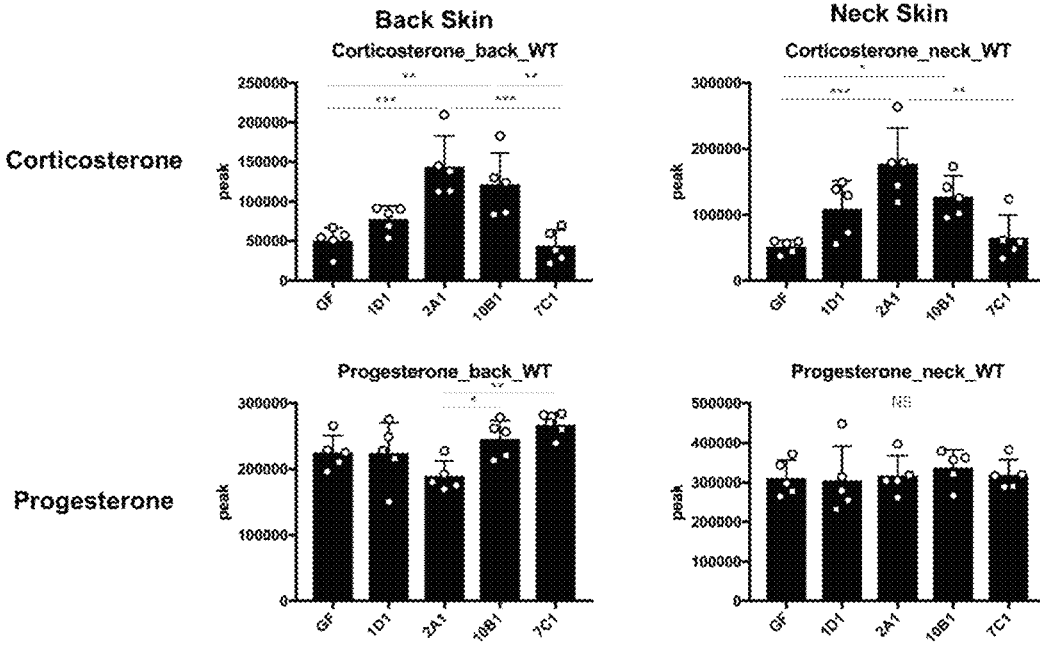

FIG. 28 shows results obtained by analyzing corticosterone and a precursor thereof, progesterone in the back skin and neck skin of germ-free B6N WT mouse inoculated with *S. cohnii* or *S. aureus*, by using gas chromatography-mass spectrometry (GC-MS) fatty acid analysis.

FIG. 29 shows results obtained by analyzing corticosterone and a precursor thereof, progesterone in the neck skin of Tmem79-KO mouse inoculated with *S. cohnii* or *S. aureus*, by using GC-MS fatty acid analysis.

DESCRIPTION OF EMBODIMENTS

The "pharmaceutical composition" according to the present invention is a pharmaceutical composition including as active components one or more substances selected from the following (a) to (d):

(a) a bacterial cell of a bacterium sensitive to ampicillin or a constituent component of the bacterium;

(b) a culture supernatant of a bacterium sensitive to ampicillin or a purified product from the culture supernatant;

(c) an extract of a bacterium sensitive to ampicillin; and (d) a metabolite of a bacterium sensitive to ampicillin.

It is preferable that the bacterium sensitive to ampicillin is also a fusidic acid-resistant bacterium. In addition, the bacterium sensitive to ampicillin is preferably a bacterium belonging to the genus *Staphylococcus*. However, it is preferable that the bacterium belonging to the genus *Staphylococcus* is not *S. aureus*. That is, as the bacterium sensitive to ampicillin, a bacterium (excluding *S. aureus*) belonging to the genus *Staphylococcus*, which is sensitive to ampicillin and further resistant to fusidic acid, is included as a particularly preferable embodiment. In this regard, in the present specification, aspects of invention other than the "pharmaceutical composition" are also described, and in a case where a bacterium sensitive to ampicillin is described also in the aspects of invention other than the "pharmaceutical composition", the bacterium described above is preferable as the bacterium sensitive to ampicillin. Further, as the aspects of invention other than the "pharmaceutical composition", quasi drugs, cosmetics, and the like are also included, and as a component of the quasi drugs, and cosmetics, the bacterium sensitive to ampicillin, and preferably a bacterium (excluding *S. aureus*) belonging to the genus *Staphylococcus*, which is sensitive to ampicillin and further resistant to fusidic acid, can be included.

<Bacterium Sensitive to Ampicillin>

The bacterium sensitive to ampicillin is preferably selected from one or more species of *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*, more preferably selected from *S. cohnii* or *S. lentus*, and most preferably *S. cohnii* selected.

Furthermore, as another embodiment of the bacterium sensitive to ampicillin, a bacterium selected from one or more species of Bacteroides sp. SA-11, *Lactobacillus reuteri, Clostridium* sp. Clone-16, *Lactobacillus johnsonii*, and *Staphylococcus arlettae* can be included. Since the bacterium and *S. cohnii* indicate a negative correlation with the exacerbation of dermatitis (high clinical scores), as shown in Experimental Example 3 to be described later, it is presumed that these bacteria also have a suppressive effect on skin inflammation similarly as in the case of *S. cohnii*.

In this regard, the bacterium may be selected from two or more species, or may be only one species selected.

Further, the 16S rDNA gene sequence of the bacterium is a sequence represented by any one of SEQ ID NOs: 1 to 7, or is preferably a sequence having 90, 91, 92, 93, 94, 95, 96, 97, 98, or 99% or more sequence identity to the sequence represented by any one of SEQ ID NOs: 1 to 7, and the 16S rDNA gene sequence is particularly preferably a sequence represented by any one of SEQ ID NOs: 1 to 7.

In the pharmaceutical composition according to the present invention, the bacterium is preferably a mouse-derived bacterium or a human-derived bacterium, and specifically, the bacterium is preferably one or more strains selected from mouse-derived bacteria deposited under Accession numbers NITE BP-02848 (SEQ ID NO: 1), NITE BP-02850 (SEQ ID NO: 2), NITE BP-02851 (SEQ ID NO: 3), NITE BP-02852 (SEQ ID NO: 4), NITE BP-02845 (SEQ ID NO: 6), and NITE BP-02847 (SEQ ID NO: 7), and a human-derived bacterium deposited under Accession number NITE BP-02853 (SEQ ID NO: 5). The above-described bacteria are each deposited with the NITE Patent Microorganisms Depositary (NPMD), Biological Resource Center, National Institute of Technology and Evaluation (address: #122, 2-5-8 Kazusakamatari, Kisarazu-shi, Chiba, Japan) on Dec. 25, 2018 (date of the original deposit).

<*S. cohnii*>

The 16S rDNA gene sequence of the *S. cohnii* is a sequence represented by any one of SEQ ID NOs: 1 to 5, or preferably a sequence having 90, 91, 92, 93, 94, 95, 96, 97, 98, or 99% or more sequence identity to the sequence represented by any one of SEQ ID NOs: 1 to 5, and the 16S rDNA gene sequence is particularly preferably a sequence represented by any one of SEQ ID NOs: 1 to 5.

In the pharmaceutical composition according to the present invention, the *S. cohnii* is preferably one or more species selected from respective strains of mouse-derived *S. cohnii* deposited under Accession numbers NITE BP-02848 (SEQ ID NO: 1), NITE BP-02850 (SEQ ID NO: 2), NITE BP-02851 (SEQ ID NO: 3), and NITE BP-02852 (SEQ ID NO: 4), and human-derived *S. cohnii* deposited under Accession number NITE BP-02853 (SEQ ID NO: 5). Further, the *S. cohnii* is preferably a human-derived strain, and accordingly, the *S. cohnii* is most preferably the above-described bacterium deposited under Accession number NITE BP-02853.

The bacterium sensitive to ampicillin may be a live bacterium or a killed bacterium, and may be a mixture of a live bacterium and a killed bacterium, and in a case where the ampicillin-sensitive bacterium is a killed bacterium, the bacterium before killed, that is, at the time point of the live bacterium is an ampicillin-sensitive bacterium. Further, in a case where the ampicillin-sensitive bacterium is a killed bacterium, the bacterium before killed, that is, at the time point of the live bacterium is preferably a fusidic acid-resistant bacterium.

<Pharmaceutical Composition>

As described above, the pharmaceutical composition according to the present invention is a pharmaceutical composition containing as active components one or more substances selected from a bacterial cell of a bacterium sensitive to ampicillin, a constituent component of the bacterium, a culture supernatant of the bacterium, a purified product from the culture supernatant, an extract of the bacterium, and a metabolite of the bacterium.

The pharmaceutical composition is preferably used for treatment, amelioration, or prevention of skin disease.

The skin disease is preferably dermatitis, and particularly preferably atopic dermatitis, dermatitis initiated by an IFN-α production promoter, dermatitis initiated by a preparation containing an imidazoquinoline derivative, or dermatitis initiated by imiquimod.

Further, the skin disease may be psoriasis, and the skin disease may be autoimmune skin disease. The autoimmune disease that may occur on the skin is not particularly limited, but specific examples of the autoimmune disease include lupus erythematosus, dermatomyositis, scleroderma, Sjogren's syndrome, and bullous disease. In this regard, the expression "treatment" includes remission and recovery of symptoms, suppression of progression and exacerbation, and the like, the expression "amelioration" includes relief and alleviation of symptoms, and the like, and the expression "prevention" includes prevention of development of new disease, and prevention of recurrence.

The pharmaceutical composition according to the present invention may contain any one of components, or two or more components among the above-described active components. Further, as the pharmaceutical composition, a substance selected from a bacterial cell of a bacterium sensitive to ampicillin, a constituent component of the bacterium, a culture supernatant of the bacterium, a purified product from the culture supernatant, an extract of the bacterium, and a metabolite of the bacterium may be used as it is, or appropriately, the pharmaceutical composition may further contain other components as needed, for example, a pharmaceutically acceptable carrier or additive agent corresponding to a dosage form, components other than the above-described specific active components that are effective for treatment or prevention of skin disease, and the like. That is, the pharmaceuticals according to the present invention can be prepared as a pharmaceutical composition containing such components.

The dosage form of the pharmaceutical composition is not particularly limited as long as it can suppress skin disease. For example, it is preferable to prepare the pharmaceutical composition as an external preparation in order to apply or paste the pharmaceutical composition for the administration, and the pharmaceutical composition may also be prepared as an internal medicine for the oral administration.

An animal species to be subjected to prescription and administration of the pharmaceutical composition includes a human, and mammals other than the human. Examples of the mammals other than a human include a mammal commonly used as a model animal for human disease and a mammal that is kept as a companion (pet), such as a mouse, a rat, a guinea pig, a rabbit, a goat, a cat, a dog, a pig, and a monkey. Therefore, the pharmaceutical composition may be prepared for the administration to a human, or may be prepared for the administration to a mammal other than the human.

The embodiment according to the administration of the pharmaceutical composition is not particularly limited as long as the desired effect of treatment, amelioration, or prevention can be obtained. That is, administration form, the number of administration times, a dosing period (frequency), and a dose of active components at one time can be appropriately adjusted in consideration of the kind of the active component to be used, the condition of the target skin disease, and the age, body weight, administration route, pharmacokinetics, and the like of a subject to be administered. In particular, in the present invention, the embodiment relating to the administration may be adjusted while grasping information such as the numbers or distribution ratios of respective bacteria in the skin normal bacterial flora.

For example, in a case where the subject to be administered is a mouse, the dose per body weight is preferably $1\times10^4$ to $1\times10^8$ CFU/g, more preferably $5\times10^3$ to $1\times10^7$ CFU/g, and particularly preferably $1\times10^4$ to $1\times10^7$ CFU/g. The number of administration times is preferably 1 to 20 times, and more preferably 1 to 10 times. The dosing period and frequency is preferably once or more per day, and the administration is preferably continued for 2 weeks or more. The administration mode such as an active component amount to a human can be appropriately adjusted through administration experiments to model animals, and the like. Further, by measuring the numbers of respective bacteria, the distribution ratios of respective bacteria, and the like in the skin normal bacterial flora, it is possible to determine a patient with skin disease to be subjected to the administration of the pharmaceutical composition according to the present invention, and it is also possible to monitor the effect of an ameliorating agent or therapeutic agent for skin disease.

<Method for Producing Pharmaceutical Composition>

One embodiment of the present invention includes a method for producing the pharmaceutical composition.

As described above, the pharmaceutical composition according to the present invention is a pharmaceutical composition containing as active components one or more substances selected from a bacterial cell of a bacterium sensitive to ampicillin or the like, a constituent component of the bacterium, a culture supernatant of the bacterium, a purified product from the culture supernatant, an extract of the bacterium, and a metabolite of the bacterium. Accordingly, the pharmaceutical composition can be produced by a common production method, for example, by obtaining the active components by a means including a technique such as suspending the bacteria to be used or a crushed product thereof at an appropriate concentration, extracting a culture supernatant by culturing the bacteria, extracting desired active components from the bacteria by an appropriate method, or separating metabolites from the bacteria or a crushed product thereof, and a culture supernatant, and further, by mixing a carrier or an additive agent, selected from, for example, an excipient, a disintegrant, a binding agent, a lubricating agent, a suspending agent, an isotonizing agent, an emulsifying agent, a sweetener, a flavor, and a coloring agent with the above-described active components to form a preparation. However, the method for producing the pharmaceutical composition is not limited to the method described above, and the pharmaceutical composition can be produced by a means including a method as long as the method can be used for obtaining a bacterial cell, a constituent component of the bacterium, a culture supernatant of the bacterium, a purified product from the culture supernatant, an extract of the bacterium, and a metabolite of the bacterium.

<Activator>

Another embodiment of the present invention includes an activator containing a bacterium that is an ampicillin-sensitive bacterium. It is preferable that the bacterium is also a fusidic acid-resistant bacterium, and it is more preferable that the bacterium sensitive to ampicillin is a bacterium (excluding *S. aureus*) belonging to the genus *Staphylococcus*, which is a fusidic acid-resistant bacterium. Further, the bacterium is particularly preferably selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus,* and *S. siinulans,* and is most preferably *S. cohnii*.

The 16S rDNA gene sequence of the bacterium is a sequence represented by any one of SEQ ID NOs: 1 to 7, or preferably a sequence having 90, 91, 92, 93, 94, 95, 96, 97, 98, or 99% or more sequence identity to the sequence represented by any one of SEQ ID NOs: 1 to 7, and the 16S rDNA gene sequence is particularly preferably a sequence represented by any one of SEQ ID NOs: 1 to 7.

Further, the bacterium is preferably one or more strains selected from respective strains of mouse-derived bacteria deposited under Accession numbers NITE BP-02848, NITE BP-02850, NITE BP-02851, NITE BP-02852, NITE BP-02845, and NITE BP-02847, and a human-derived bacterium deposited under Accession number NITE BP-02853. Moreover, the bacterium is preferably the ones described in the above paragraphs of <*S. cohnii*>.

The activator is used for applications such as treatment of the skin disease of the bacterium sensitive to ampicillin as described above, amelioration of the skin disease, prevention of the skin disease, proliferation of the bacterium, and amelioration of skin condition, but is not particularly limited thereto. The activator has at least one or more effects selected from an effect on the treatment of skin disease, an effect on amelioration of skin disease, an effect on prevention of skin disease, an effect on proliferation of the bacterium, and an effect on amelioration of skin condition, and due to such effects, the activator can be used as a component of, for example, the above-described pharmaceutical composition, a quasi drug, or cosmetics.

It is preferable that the activator further contains a steroid biosynthesis-related protein as an active component. Herein, the expression "steroid biosynthesis-related protein" is a generic term for proteins (enzymes) involved in steroid biosynthesis, and the steroid biosynthesis-related protein is preferably a protein involved in synthesis of squalene that is a steroid intermediate. Accordingly, the steroid biosynthesis-related protein is preferably squalene synthase.

Further, the activator that exerts an effect of activating the effect of a bacterium sensitive to ampicillin is preferably an activator containing an anti-*S. aureus* antibody as an active component.

In this regard, it can be determined whether the proliferation of bacteria occurs, by a known technique, for example, by measuring the number (CFU/g) of bacteria in a sample scraped from the skin with the use of a common technique and determining whether or not the measured value is statistically significantly higher than that of a healthy subject at normal time.

<Inhibitor of *S. aureus*>

Another embodiment of the present invention includes an inhibitor of *S. aureus*. The active component of the inhibitor is not particularly limited as long as it exerts an action of suppressing the proliferation of *S. aureus*, but it is undesirable to use as the inhibitor a substance that kills *S. aureus* by physically or chemically acting on the bacterium and decomposing or dissolving the bacterium, because an inflammatory effect may be initiated on the host by the decomposition of bacterial cells of the bacterium, and dermatitis may be exacerbated. Accordingly, as the active component, a component containing an anti-*S. aureus* antibody that attacks and kills *S. aureus* by the immune mechanism of a living body is preferable, and a component containing one or more substances selected from a bacterial cell of an ampicillin-sensitive bacterium, a constituent component of the bacterium, a culture supernatant of the bacterium, a purified product from the culture supernatant, an extract of the bacterium, and a metabolite of the bacterium is preferable. Further, the inhibitor may contain as an active component only any one kind of the anti-*S. aureus* antibody, a bacterial cell of an ampicillin-sensitive bacterium, a constituent component of the bacterium, a culture supernatant of the bacterium, and a purified product from the culture supernatant, an extract of the bacterium, and a metabolite of the bacterium, or may contain together as active components one or more substances selected from an anti-*S. aureus* antibody, a bacterial cell of an ampicillin-sensitive bacterium, a constituent component of the bacterium, a culture supernatant of the bacterium, a purified product from the culture supernatant, an extract of the bacterium, and a metabolite of the bacterium. In addition, the bacterium sensitive to ampicillin is more preferably a fusidic acid-resistant bacterium, and furthermore preferably a bacterium (excluding *S. aureus*) belonging to the genus *Staphylococcus*, which is a fusidic acid-resistant bacterium. For example, specifically, the bacterium sensitive to ampicillin is preferably selected from one or more species of *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*, and is in particular, more preferably *S. cohnii*. Further, it is also preferable that the active component is an anti-*S. aureus* antibody. As the specific effect exerted by an action of suppressing proliferation of *S. aureus* in the inhibitor of *S. aureus*, an effect of activating the effect on treatment, amelioration, or prevention of skin disease, an effect of proliferating the bacterium, an effect of ameliorating skin condition, or the like can be included, but the specific effect is not particularly limited thereto. Because of such effects, the inhibitor of *S. aureus* can be used as a component in, for example, the above-described pharmaceutical composition, a quasi drug, or cosmetics.

<Therapeutic Agent for Skin Disease>

Another embodiment of the present invention includes a therapeutic agent for skin disease containing one or more substances selected from a bacterial cell of a bacterium sensitive to ampicillin, a constituent component of the bacterium, a culture supernatant of the bacterium, a purified product from the culture supernatant, an extract of the bacterium, and a metabolite of the bacterium. The bacterium sensitive to ampicillin is preferably resistant to fusidic acid, and is more preferably a bacterium (excluding *S. aureus*) belonging to the genus *Staphylococcus*, which is resistant to fusidic acid. Specifically, such a bacterium is particularly preferably selected from one or more species of, for example, *S. epidermidis*, *S. capitis*, *S. lentus*, *S. caprae*, *S.*

*saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*, and among them, more preferably *S. cohnii* selected.

The 16S rDNA gene sequence of the bacterium is a sequence represented by any one of SEQ ID NOs: 1 to 7, or preferably a sequence having 90, 91, 92, 93, 94, 95, 96, 97, 98, or 99% or more sequence identity to the sequence represented by any one of SEQ ID NOs: 1 to 7, and the 16S rDNA gene sequence is particularly preferably a sequence represented by any one of SEQ ID NOs: 1 to 7.

Further, the bacterium is preferably one or more strains selected from respective strains of mouse-derived bacteria deposited under Accession numbers NITE BP-02848, NITE BP-02850, NITE BP-02851, NITE BP-02852, NITE BP-02845, and NITE BP-02847, and a human-derived bacterium deposited under Accession number NITE BP-02853. Moreover, the bacterium is preferably the ones described in the above paragraphs of <*S. cohnii*>.

<Method for Suppressing Proliferation of *S. aureus*>

Another embodiment of the present invention includes a method for suppressing proliferation of *S. aureus* by using a substance containing one or more substances selected from an anti-*S. aureus* antibody, a bacterial cell of a bacterium sensitive to ampicillin, a constituent component of the bacterium, a culture supernatant of the bacterium, a purified product from the culture supernatant, an extract of the bacterium, and a metabolite of the bacterium. The bacterium sensitive to ampicillin is preferably also a fusidic acid-resistant bacterium, and more preferably a bacterium (excluding *S. aureus*) belonging to the genus *Staphylococcus*, which is sensitive to ampicillin and fusidic acid-resistant bacterium. Specifically, the bacterium sensitive to ampicillin is particularly preferably selected from one or more species of, for example, *S. epidermidis*, *S. capitis*, *S. lentus*, *S. caprae*, *S. saccharolyticus*, *S. warneri*, *S. pasteuri*, *S. haemolyticus*, *S. homonis*, *S. lugdunesis*, *S. auricularis*, *S. saprophyticus*, *S. cohnii*, *S. xylosus*, and *S. siinulans*, and is most preferably *S. cohnii*. A more preferable embodiment includes a method for suppressing proliferation of *S. aureus*, including applying onto an affected part one or more substances selected from, for example, a bacterial cell of a bacterium of *S. cohnii*, a constituent component of the bacterium, a culture supernatant of the bacterium, a purified product from the culture supernatant, an extract of the bacterium, and a metabolite of the bacterium.

The 16S rDNA gene sequence of the bacterium is a sequence represented by any one of SEQ ID NOs: 1 to 7, or preferably a sequence having 90, 91, 92, 93, 94, 95, 96, 97, 98, or 99% or more sequence identity to the sequence represented by any one of SEQ ID NOs: 1 to 7, and the 16S rDNA gene sequence is particularly preferably a sequence represented by any one of SEQ ID NOs: 1 to 7.

Further, the bacterium is preferably one or more strains selected from respective strains of mouse-derived bacteria deposited under Accession numbers NITE BP-02848, NITE BP-02850, NITE BP-02851, NITE BP-02852, NITE BP-02845, and NITE BP-02847, and a human-derived bacterium deposited under Accession number NITE BP-02853. Moreover, the bacterium is preferably the ones described in the above paragraphs of <*S. cohnii*>.

A specific embodiment includes, for example, applying the above-described substances or pasting the substances together with an appropriate carrier onto a lesion site in the skin of a living body having skin disease.

<Method for Enhancing Transcription of Glucocorticoid-Responsive Gene>

Another embodiment of the present invention includes a method for enhancing transcription of a glucocorticoid-responsive gene, using one or more substances selected from a bacterial cell of an ampicillin-sensitive bacterium, a constituent component of the bacterium, a culture supernatant of the bacterium, a purified product from the culture supernatant, an extract of the bacterium, and a metabolite of the bacterium. The ampicillin-sensitive bacterium is preferably a fusidic acid-resistant bacterium, and more preferably a bacterium (excluding *S. aureus*) belonging to the genus *Staphylococcus*. Specifically, the ampicillin-sensitive bacterium is preferably selected from one or more species of, for example, *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans*, and is more preferably one or more species of *S. cohnii* and *S. lentus*. Further, the glucocorticoid-responsive gene is preferably one or more genes of Fkbp5, Zbtb16, and Tsc22d3. Furthermore, the glucocorticoid-responsive gene is preferably a gene encoding a steroid biosynthesis-related protein, and in this case, the steroid biosynthesis-related protein is preferably squalene synthase.

A transcription product of a glucocorticoid-responsive gene can be increased by using several methods known in the technical field to which the invention belongs. Typically, the transcription of the gene may be enhanced by applying the constituent component and the like of the bacterium to a target animal or the like, or the transcription of the gene may be enhanced by administering a recombinant expression vector prepared by using a nucleic acid extracted from the bacterium to a target animal or the like.

<Analysis Method of Flora>

Another embodiment of the present invention further includes a method for analyzing flora present on the skin of a living organism having skin disease. The method is not particularly limited as long as it is a method commonly used as a method for analyzing flora of the skin, and is performed by a technique such as culturing a sample scraped from the skin of a target living organism with, for example, a cotton swab or the like in an appropriate culture medium. In addition, the biological species to be targeted is not particularly limited, and can be selected from a human or an animal other than the human.

In a case where an animal other than a human is selected as the living organism having skin disease, for example, a model animal with skin disease can be selected. As the model animal with skin disease, specifically, a Tmem79$^{-/-}$ mouse (Tmem79-KO mouse) can be included. Further, as the model animal with skin disease, a specific pathogen-free (SPF) animal is suitable, and typically, a SPF Tmem79$^{-/-}$ mouse (SPF-Tmem79-KO mouse) is most suitably selected. In addition, in a case where a human is selected, for example, a patient affected by skin disease can be selected.

Further, specific examples of the skin disease include dermatitis, atopic dermatitis, dermatitis initiated by an IFN-α production promoter, dermatitis initiated by a pharmaceutical preparation containing an imidazoquinoline derivative, dermatitis initiated by imiquimod, psoriasis, and autoimmune skin disease.

<Method for Assisting Selection of Treatment Method>

One embodiment using the method for analyzing flora according to the present invention includes a method for assisting selection of a treatment method for a living organism having skin disease, including the steps of: (1) calculating a ratio of *S. aureus* to skin normal bacterial flora in a skin sample collected from a disease site of the living organism; and (2) in a case where the ratio is higher than a reference value, selecting a pharmaceutical composition containing as active components one or more substances selected from the following (a) to (d):

(a) a bacterial cell of a bacterium sensitive to ampicillin or a constituent component of the bacterium;

(b) a culture supernatant of a bacterium sensitive to ampicillin or a purified product from the culture supernatant;

(c) an extract of a bacterium sensitive to ampicillin; and (d) a metabolite of a bacterium sensitive to ampicillin.

As the reference value, (i) an average value of ratios of *S. aureus* to skin normal bacterial flora in skin samples of individuals having no skin disease (healthy subjects in a case where the living organism having skin disease is a human), which are living organisms of the same species as the living organism having skin disease, (ii) a ratio of *S. aureus* to skin normal bacterial flora in a skin sample collected from a site other than the disease site of the living organism having skin disease, or the like can be used.

The ampicillin-sensitive bacterium is preferably a fusidic acid-resistant bacterium, and is more preferably a bacterium (excluding *S. aureus*) belonging to the genus *Staphylococcus*, which is resistant to fusidic acid. Specifically, the ampicillin-sensitive bacterium is particularly preferably selected from one or more species of, for example, *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus*, and *S. siinulans*, and is most preferably *S. cohnii*.

According to this method, for example, a person other than doctors can calculate ratios of components in a skin sample collected from a disease site of a living organism having skin disease, and can provide as the auxiliary information a doctor with the results obtained by comparing the calculated ratios to arbitrary reference values and the information about which pharmaceutical composition should be preferably selected, and as a result which, by using such auxiliary information, the doctor can determine a treatment method to be practically performed, for example, which pharmaceutical composition should be administered in what amount with what dosage form, and the like.

<Method for Obtaining Auxiliary Information>

One embodiment using the method for analyzing flora according to the present invention includes a method for obtaining auxiliary information about treatment of skin disease in a living organism having skin disease. The method includes the steps of: (1) calculating a ratio of *S. aureus* to skin normal bacterial flora in a skin sample collected from a living organism having skin disease before treatment of the skin disease; (2) calculating a ratio of *S. aureus* to skin normal bacterial flora in a skin sample collected from a living organism having skin disease after treatment of the skin disease; and (3) comparing the ratio calculated in step (1) with the ratio calculated in step (2). According to this method, for example, a person other than doctors can provide a doctor with the results obtained by calculating ratios of *S. aureus* in skin normal bacterial flora before and after treatment and comparing the ratios between before and after treatment, as the auxiliary information of treatment, and as a result of which the doctor can determine the course of the undergone treatment of skin disease, for example, amelioration, exacerbation, and the like of the disease state, by using the auxiliary information.

<Anti-*S. aureus* Antibody and Steroid Biosynthesis-Related Protein>

Another embodiment of the present invention includes an anti-*S. aureus* antibody and/or a steroid biosynthesis-related protein for use in treatment of skin disease, use of one or more substances selected from an anti-*S. aureus* antibody and a steroid biosynthesis-related protein for producing a medicine for treatment of skin disease, and a method for treatment of skin disease including administering to a patient one or more substances selected from an anti-*S. aureus* antibody and a steroid biosynthesis-related protein. Further, one embodiment of the present invention includes a bacterial cell of a bacterium sensitive to ampicillin for use in treatment of skin disease, a constituent component of the bacterium, a culture supernatant of the bacterium, a purified product from the culture supernatant, an extract of the bacterium, or a metabolite of the bacterium. In this case, the bacterium sensitive to ampicillin is preferably a fusidic acid-resistant bacterium, and more preferably a bacterium (excluding *S. aureus*) belonging to the genus *Staphylococcus*, which is a fusidic acid-resistant bacterium. Specifically, for example, the bacterium sensitive to ampicillin is particularly preferably selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus,* and *S. siinulans.*

The anti-*S. aureus* antibody is not particularly limited as long as it specifically binds to *S. aureus,* and as the anti-*S. aureus* antibody, for example, any isotype antibody may be used, and in particular, an immunoglobulin G (IgG) antibody is suitably used. Further, the anti-*S. aureus* antibody is not required to have the full length as in the case of a natural antibody as long as it specifically binds to *S. aureus,* and may also be an antibody fragment or a derivative, or a chimeric antibody (such as a humanized antibody). Furthermore, the anti-*S. aureus* antibody may also be a bispecific antibody, or a multifunctional antibody such as an antibody-drug conjugate (ADC) with a payload bound to the antibody via a linker. In this regard, the species of an animal (immunized animal) producing an antibody is not particularly limited, and may be selected from a mouse, a rat, a guinea pig, a rabbit, a goat, a sheep, and the like as in the conventional case.

The expression "steroid biosynthesis-related protein" is a generic term for proteins involved in steroid biosynthesis, and squalene is suitably used in the present invention.

<Use in Treatment, Use for Producing Medicine for Treatment, and Treatment Method>

Another embodiment of the present invention includes a bacterial cell of a bacterium sensitive to ampicillin for use in treatment of skin disease, a constituent component of the bacterium, a culture supernatant of the bacterium, a purified product from the culture supernatant, an extract of the bacterium, or a metabolite of the bacterium. The bacterium sensitive to ampicillin is preferably a fusidic acid-resistant bacterium, and more preferably a bacterium (excluding *S. aureus*) belonging to the genus *Staphylococcus,* which is resistant to fusidic acid. Specifically, the bacterium sensitive to ampicillin is preferably a bacterial cell of a bacterium selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus,* and *S. siinulans,* a constituent component of the bacterium, a culture supernatant of the bacterium, a purified product from the culture supernatant, an extract of the bacterium, or a metabolite of the bacterium, and particularly preferably a bacterial cell of a bacterium of *S. cohnii,* a constituent component of the bacterium, a culture supernatant of the bacterium, a purified product from the culture supernatant, an extract of the bacterium, or a metabolite of the bacterium.

Further, another embodiment of the present invention includes use of one or more substances selected from a bacterial cell of a bacterium sensitive to ampicillin for producing a medicine for treatment of skin disease, a constituent component of the bacterium, a culture supernatant of the bacterium, a purified product from the culture supernatant, an extract of the bacterium, and a metabolite of the bacterium, and the bacterium sensitive to ampicillin is preferably a fusidic acid-resistant bacterium, and more preferably a bacterium (excluding *S. aureus*) belonging to the genus *Staphylococcus,* which is resistant to fusidic acid. Specifically, the bacterium sensitive to ampicillin is preferably a bacterial cell of a bacterium selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus,* and *S. siinulans,* a constituent component of the bacterium, a culture supernatant of the bacterium, a purified product from the culture supernatant, an extract of the bacterium, or a metabolite of the bacterium. In particular, use of one or more substances selected from a bacterial cell of *S. cohnii,* a constituent component of the bacterium, a culture supernatant of the bacterium, a purified product from the culture supernatant, an extract of the bacterium, and a metabolite of the bacterium is particularly preferable.

Furthermore, another embodiment of the present invention includes a method for treatment of skin disease by administering to a patient one or more substances selected from a bacterial cell of an ampicillin-sensitive bacterium, a constituent component of the bacterium, a culture supernatant of the bacterium, a purified product from the culture supernatant, an extract of the bacterium, and a metabolite of the bacterium. The bacterium sensitive to ampicillin is preferably a fusidic acid-resistant bacterium, and more preferably a bacterium (excluding *S. aureus*) belonging to the genus *Staphylococcus,* which is resistant to fusidic acid. Specifically, the bacterium sensitive to ampicillin is preferably a bacterial cell of a bacterium selected from one or more species of *S. epidermidis, S. capitis, S. lentus, S. caprae, S. saccharolyticus, S. warneri, S. pasteuri, S. haemolyticus, S. homonis, S. lugdunesis, S. auricularis, S. saprophyticus, S. cohnii, S. xylosus,* and *S. siinulans,* a constituent component of the bacterium, a culture supernatant of the bacterium, a purified product from the culture supernatant, an extract of the bacterium, or a metabolite of the bacterium. In particular, it is preferable to use a method for treatment of skin disease by administering to a patient a substance selected from one or more substances selected from a bacterial cell of a bacterium of *S. cohnii,* a constituent component of the bacterium, a culture supernatant of the bacterium, a purified product from the culture supernatant, an extract of the bacterium, or a metabolite of the bacterium.

The bacterium in the use in treatment of skin disease, the use for producing a medicine for treatment of skin disease, or the method for treatment of skin disease has a 16S rDNA gene sequence represented by any one of SEQ ID NO: 1 to 7, or preferably a sequence having 90, 91, 92, 93, 94, 95, 96, 97, 98, or 99% or more sequence identity to the sequence represented by any one of SEQ ID NOs: 1 to 7, and the 16S rDNA gene sequence is particularly preferably a sequence represented by any one of SEQ ID NOs: 1 to 7.

Further, the bacterium is preferably one or more strains selected from respective strains of mouse-derived bacteria deposited under Accession numbers NITE BP-02848, NITE BP-02850, NITE BP-02851, NITE BP-02852, NITE BP-02845, and NITE BP-02847, and a human-derived bacterium deposited under Accession number NITE BP-02853. Moreover, the bacterium is preferably the ones described in the above paragraphs of <S. cohnii>.

<Bacterium Strain>

Another embodiment of the present invention includes a bacterium strain belonging to the species S. cohnii specified by any one of Accession numbers NITE BP-02848, NITE BP-02850, NITE BP-02851, NITE BP-02852, and NITE BP-02853.

<Bacterium>

The bacterium of the present invention, which is an embodiment different from that of the bacterium sensitive to ampicillin, includes a bacterium selected from one or more species of Methylobacterium sp. RD4.1, Methylobacterium sp. SKJH-1, Mesorhizobium alhagi, Sphingomonas sp. MK355, Sphingomonas sp. AC83, Pantoea sp. lan5, Weissella cibaria, Bradyrhizobium sp. STM 3843, Lactococcus lactis, Afipia genosp.1, Methylobacterium populi, Sediminibacterium sp. IV-37, Bradyrhizobium sp. Aust13C, Pelomonas saccharophila, Bradyrhizobium sp. Shinshu-th2, Methylobacterium sp. BF15, and Bradyrhizobium sp. BTAi1. Since the bacterium and S. cohnii indicate a negative correlation with the exacerbation of dermatitis (high clinical scores), as shown in Experimental Example 3 to be described later, it is presumed that these bacteria also have a suppressive effect on skin inflammation similarly as in the case of S. cohnii. For this reason, these bacteria can be used for various kinds of applications similarly to the bacteria described in the above <Bacterium sensitive to ampicillin>.

EXAMPLES

Next, the present invention will be described in more detail with reference to Examples, however, the present invention is not limited to the following Examples.

In this regard, the clone name, derivation, species, accession number, and sequence number of each of the clones used in the present Examples are shown in Table 1. The bacteria are each deposited with the NITE Patent Microorganisms Depositary (NPMD), Biological Resource Center, National Institute of Technology and Evaluation (address: #122, 2-5-8 Kazusakamatari, Kisarazu-shi, Chiba, Japan) on Dec. 25, 2018 (date of the original deposit).

TABLE 1

| Clone | Origin of bacterium | Species | Accession number | SEQ ID NO: |
|-------|---------------------|---------|------------------|------------|
| 2A1   | Mouse | S. Cohnii | NITE BP-02848 | 1 |
| 7B1   | Mouse | S. Cohnii | NITE BP-02850 | 2 |
| 7C1   | Mouse | S. Cohnii | NITE BP-02851 | 3 |
| 7F1   | Mouse | S. Cohnii | NITE BP-02852 | 4 |
| 10B1  | Human | S. Cohnii | NITE BP-02853 | 5 |
| 1B2   | Mouse | S. epidermidis | NITE BP-02845 | 6 |
| 1H2   | Mouse | S. lentus | NITE BP-02847 | 7 |
| 1D1   | Mouse | S. aureus | NITE BP-02846 | 8 |
| 2G3   | Mouse | C. mastitidis | NITE BP-02849 | 9 |

Preparation Example 1

<Preparation of Tmem79-KO Mouse>

Mouse ES cells of Project ID: CSD74985 and Allele: Tmem79tm1Wtsi Deletion were obtained from the Knockout Mouse Project (KOMP) (www.komp.org/) of the UC DAVIS repository. The mutant cells were individuated to obtain a chimeric mouse in the individuation service for cryopreserved mouse resources of the Federation of International Mouse Resources (FIMRe) (RIKEN BRC) (mus.br-c.riken.jp/ja/mailnews/20080605#mn/20080604#2). The obtained mutant individual was repeatedly mated with C57/BL6N mice to obtain a homozygous Tmem79-KO mouse. The identification of the Tmem79-KO mouse was performed on the basis of the confirmation of the mutant Tmem79 gene by PCR, and the comparison of differences in the skin condition by visual inspection.

Experimental Example 1

(Dermatitis Clinical Score in Tmem79-KO Mouse)

The Tmem79-KO mouse was prepared as in Preparation Example 1 and raised under the specific pathogen-free (SPF) environment (SPF-Tmem79-KO mouse).

Figure 1:
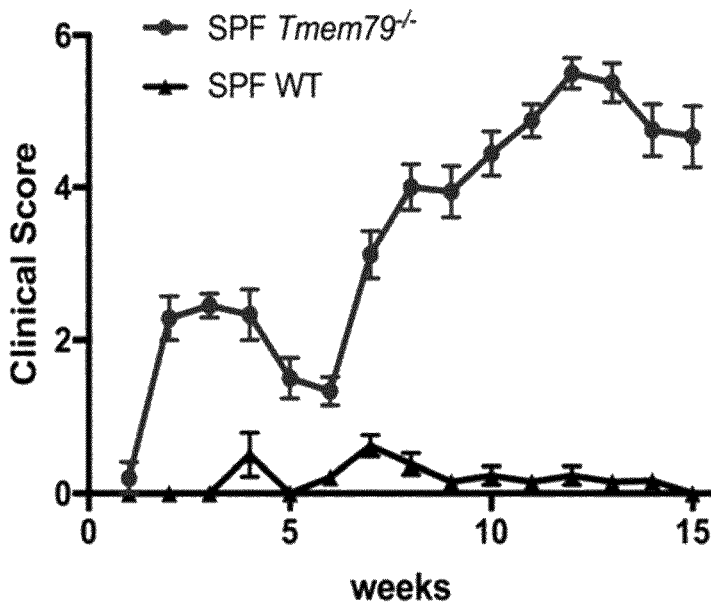
FIG. 1 shows a graph with time of clinical scores in the skins of wild-type (WT) SPF mice (SPF-WT mice) and SPF-Tmem79$^{-/-}$ mice.

For the SPF-Tmem79-KO mouse and the control (SPF-WT mice), the clinical scores were evaluated on a 4-point scale of 0: normal, 1: mild, 2: moderate, and 3: severe for each of the four items of erythema, edema, erosion, and dryness. The degree of inflammation in the skin was evaluated by using the total value of the clinical scores of the four items. The state of the changes of the clinical scores is shown in FIG. 1. In the drawing, the SPF-Tmem79-KO mouse is described as "SPF Tmem79$^{-/-}$", and the SPF-WT mouse is described as "SPF WT". It can be understood that the SPF-Tmem79-KO mouse developed bimodal dermatitis.

Experimental Example 2

(Changes in Flora at Lesion Site of SPF-Tmem79-KO Mouse)

As described above, the SPF-Tmem79-KO mouse developed bimodal dermatitis, and in particular, in the latter half of the disease stage, it was observed that dermatitis was spread around the neck.

The identification of bacterial species and the analysis of species composition were performed by meta-16S analysis of bacterial flora, by using a skin sample collected from a SPF-Tmem79-KO mouse at each postnatal period by scraping a lesion site in the skin of the mouse with the use of a cotton swab immersed in phosphate-buffered saline (PBS). The results are shown in FIG. 2.

In the flora of the SPF-Tmem79-KO mouse, it was found that the expression of S. aureus was increased with the exacerbation of dermatitis, and further, the proportion of S. cohnii was increased in the mouse during the age of 5 to 6 weeks of which the dermatitis was temporarily suppressed. On the other hand, S. aureus was hardly detected in the skins of wild-type mice (SPF-WT).

Experimental Example 3

(Clinical Score and Flora Distribution)

Figure 3:
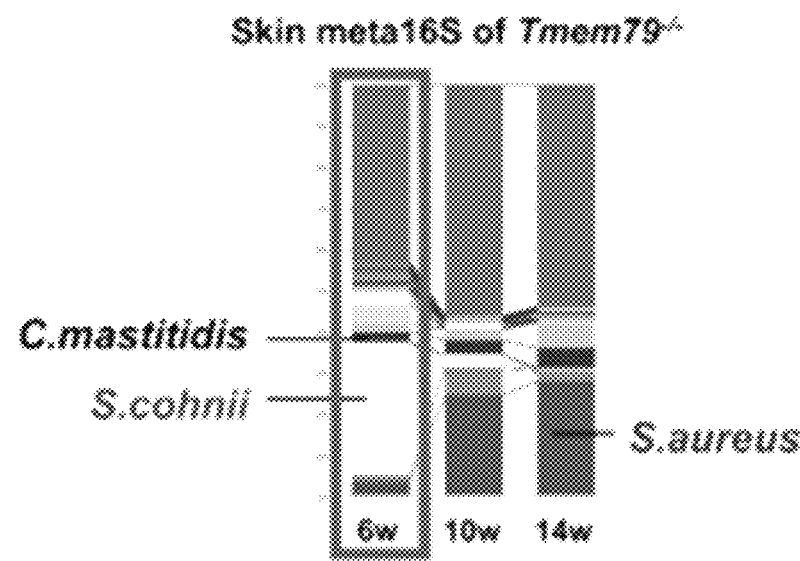
FIG. 3A shows results of meta-16S analysis of bacterial flora, performed by using the skins of SPF-Tmem79$^{-/-}$ mice.
FIG. 3B shows results of meta-16S analysis of bacterial flora, performed by using the skins of SPF-Tmem79$^{-/-}$ mice, and results of correlation analysis of Spearman using clinical scores, and a list of bacteria that are inversely correlated with the exacerbation of dermatitis (high clinical scores).

Flora analysis (meta-16S analysis) of skin samples of the SPF-Tmem79-KO mouse obtained by the technique similar to that in the above was performed (FIG. 3A), and Spearman correlation analysis was performed by using the results and the clinical scores of the mice. The results are shown in FIG. 3B.

It can be understood that S. aureus showed a strong positive correlation with the exacerbation of dermatitis (high clinical scores). On the other hand, *S. cohnii* showed a negative correlation, and thus it was suggested that *S. cohnii* had a suppressive effect on skin inflammation. Further, similarly as in the case of *S. cohnii, Bacteroides* sp. SA-11, *Lactobacillus reuteri, Methylobacterium* sp. RD4.1, *Methylobacterium* sp. SKJH-1, *Mesorhizobium alhagi, Sphingomonas* sp. MK355, *Sphingomonas* sp. AC83, *Clostridium* sp. Clone-16, *Pantoea* sp. lan5, *Weissella cibaria, Bradyrhizobium* sp. STM 3843, *Lactococcus lactis, Afipia* genosp.1, *Lactobacillus johnsonii, Methylobacterium populi, Staphylococcus arlettae, Sediminibacterium* sp. IV-37, *Bradyrhizobium* sp. Aust13C, *Pelomonas saccharophila, Bradyrhizobium* sp. Shinshu-th2, *Methylobacterium* sp. BF15, and *Bradyrhizobium* sp. BTAi1 also showed a negative correlation, and therefore, it is presumed that these bacteria also have a suppressive effect on skin inflammation.

The correlation coefficient and the significant difference test were calculated by using GraphPad Prism software with two-tailed unpaired Student's t-test.

Experimental Example 4

(Gene Analysis of SPF-Tmem79-KO Mouse)

Figure 4:
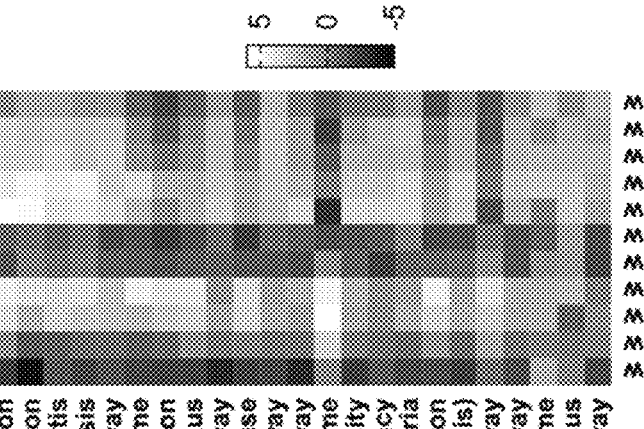
FIG. 4 shows results of pathway analysis performed by using RNAs extracted from the skins of SPF-WT mice and SPF-Tmem79$^{-/-}$ mice.

Skin samples were obtained from the skins of SPF-Tmem79-KO mouse and SPF-WT mice during the age of 1 to 15 weeks by the technique similar to that in Experimental Example 2, and pathway analysis of RNA-seq gene expression was performed on the skin samples. The results are shown in FIG. 4. The gene expression involved in various immune responses was enhanced with the increase of the above-described clinical scores (exacerbation of dermatitis) in the SPF-Tmem79-KO mouse, and the gene expression involved in immune response such as cytokine receptor signaling or T-cell receptor signaling of the SPF-Tmem79-KO mouse during the age of 5 to 6 weeks, of which the proportion of *S. cohnii* was high and the dermatitis was temporarily alleviated, was suppressed.

IL-17A is an interleukin that acts on a wide range of cells such as fibroblasts, epithelial cells, vascular endothelial cells, or macrophages, and induces inflammation by being involved in induction of inflammatory cytokines and chemokines such as IL-6 and TNF-α, migration of neutrophils, or the like.

Figure 5:
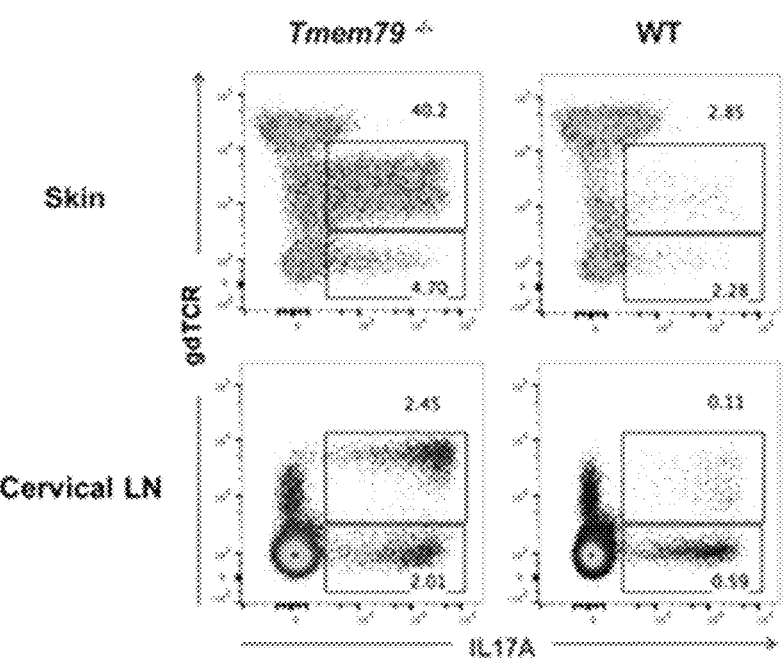
FIG. 5 shows results of fluorescence-activated cell sorting (FACS) analysis using T cells of the skins (Skin) and cervical lymph nodes (Cervical LN) of SPF-WT mice and SPF-Tmem79$^{-/-}$ mice.

Further, from the results (FIG. 5) of FACS analysis using the skins and cervical lymph node T cells of SPF-Tmem79-KO mouse and SPF-WT mice during the age of 10 to 12 weeks, it was confirmed that the IL-17A-producing T cells were increased in both of the skins and lymph nodes of the SPF-Tmem79-KO mouse.

From the results described above, it was confirmed that the SPF-Tmem79-KO mouse developed bimodal dermatitis, immune response at a cellular level and a genetic level was caused with the dermatitis, and the immune response was initiated in both of the skin and the lymph node.

Figure 6:
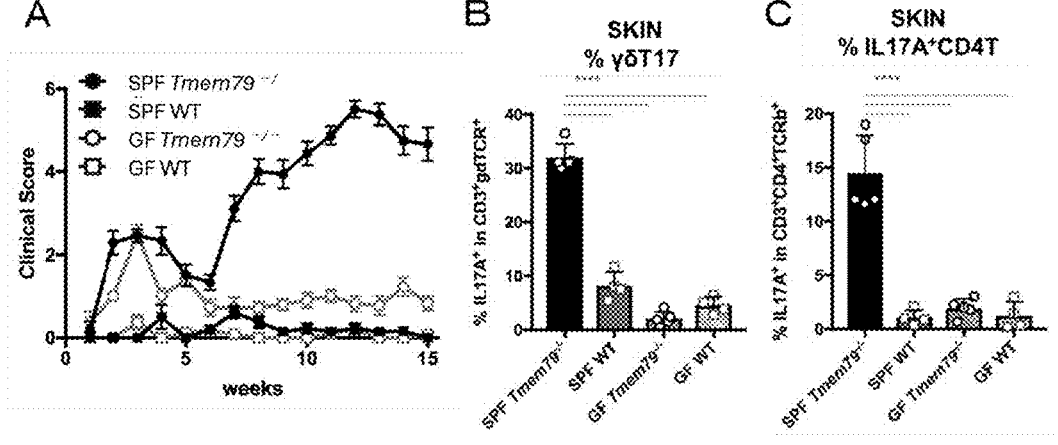
FIG. 6A is a graph that indicates changes over time of clinical scores in the skins of SPF-Tmem79$^{-/-}$ mice, SPF-WT mice, Tmem79$^{-/-}$ mice (GF-Tmem79$^{-/-}$ mice) under the germ-free (GF) environment, and GF-WT mice.
FIGS. 6B and 6C are graphs that indicate the proportions of γδ T cells and CD4 T cells in interleukin-17A (IL-17A)-producing T cells, respectively in respective mice.

Further, according to the evaluation of the clinical scores, the development of dermatitis in the Tmem79-KO mouse under the germ-free (GF) environment (GF-Tmem79-KO mouse), the wild-type mice under the GF environment (GF-WT mice), and the SPF-WT mice was suppressed (FIG. 6A), and in the skins of these mice, the induction of IL-17A-producing T cells in γδ T-cell population(=CD3+ gdTCR cells) (FIG. 6B), or the induction of IL-17A-producing T cells in CD4 T cells(=CD3+CD4+TCR cells) (FIG. 6C) was not observed.

(Analysis of Acquired Immunodeficient Tmem79-KO Mouse)

A Tmem79-KO mouse was mated with a Rag2 KO mouse (available from The Jackson Laboratory) to prepare an acquired immunodeficient Tmem79-KO mouse (Rag2$^{-/-}$ Tmem79$^{-/-}$ mouse).

Figure 7:
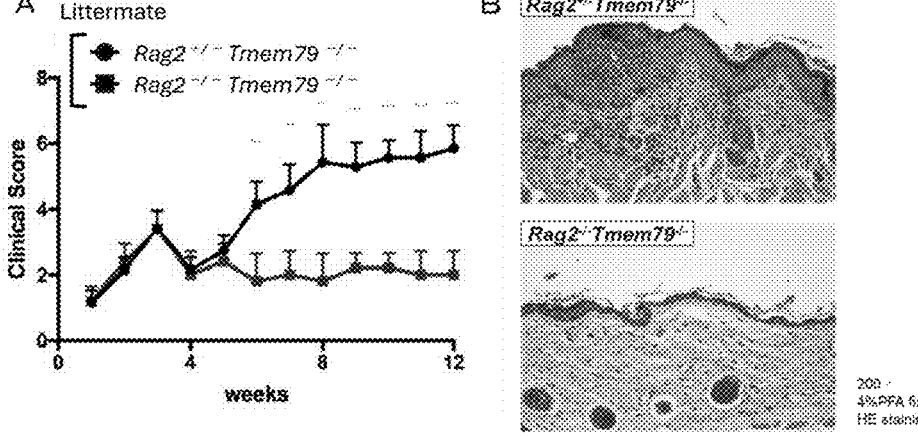
FIG. 7A is a graph that indicates changes over time of clinical scores using the skins in RAG2-knockout (Rag2$^{-/-}$) and Tmem79$^{-/-}$ mice (acquired immunodeficient Tmem79$^{-/-}$ mice), and Rag2$^{-/-}$ and Tmem79$^{-/-}$ mice.
FIG. 7B shows microscope images of histopathologic examination of the skins of respective mice by histo-staining.

The clinical scores were obtained by the technique similar to that in Experimental Example 1 (FIG. 7A), and further histopathologic examination in the skins of the mice during the age of 10 to 12 weeks was performed (FIG. 7B).

From the clinical scores and also from the results of the histopathologic examination, it was found that the development of dermatitis in the latter half, which was observed in a Tmem79-KO mouse, was suppressed in the acquired immunodeficient Tmem79-KO mouse, and it was suggested that the acquired immunity played an important role in the latter half of the exacerbation of bimodal dermatitis of the Tmem79-KO mouse.

Preparation Example 2

(Preparation of Gnotobiotic Mouse)

Skin tissues collected by scraping the skin of a SPF mouse with a cotton swab immersed in 1 mL of phosphate-buffered saline (PBS) or brain heart infusion (BHI) were cultured under aerobic conditions by using multiple culture media (such as mannitol salt agar with egg yolk, and tryptic soy agar), and *S. aureus, S. epidermidis,* and *S. lentus* were isolated by determining the 16S rDNA sequence of the obtained single colony and identifying the bacterial species. In this regard, the *S. aureus* isolated here is a strain named BP-02846, the *S. epidermidis* isolated here is a strain named BP-02845, and the *S. lentus* isolated here is a strain named BP-02847.

Each of the isolated bacteria was cultured in BHI overnight, and a single bacterium was inoculated in the skin of a GF-Tmem79-KO mouse by applying with a cotton swab a culture medium of which the amount of bacteria had been adjusted to $2.0 \times 10^6$ CFU.

Experimental Example 5

(Induction of Dermatitis in Gnotobiotic Tmem79-KO Mouse)

By using a gnotobiotic Tmem79-KO mouse, which was prepared with the *S. aureus, S. epidermidis,* or *S. lentus* prepared in Preparation Example 2, it was examined whether the dermatitis was able to be induced by skin normal bacteria, or whether the bacterium inducing the dermatitis was only a specific bacterium.

As the control, a GF-Tmem79-KO mouse (conventionalized mouse) co-housed with a SPF-Tmem79-KO mouse was used.

Figure 8:
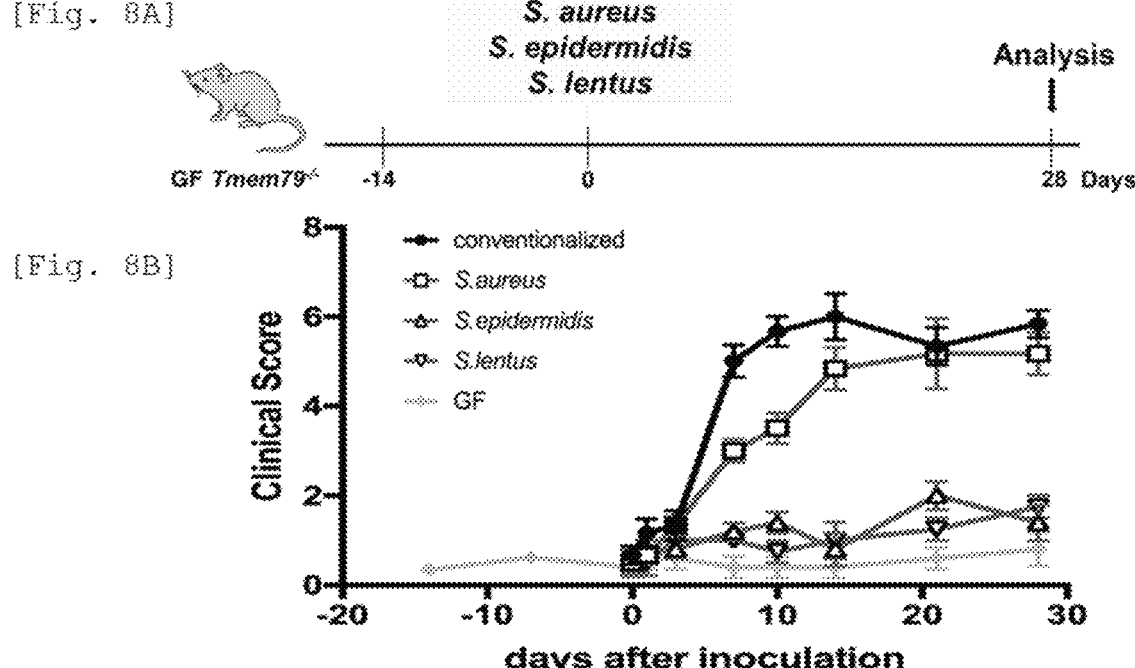
FIG. 8A is a schematic diagram showing an experimental flow.
FIG. 8B is a graph that indicates changes over time of clinical scores in the skins of gnotobiotic Tmem79$^{-/-}$ mice prepared by *S. aureus*, *S. epidermidis*, or *Staphylococcus lentus* (*S. lentus*).

The conventionalized mouse, and the gnotobiotic Tmem79-KO mouse to which $2.0 \times 10^6$ CFU of *S. aureus* had been applied developed dermatitis, but the gnotobiotic SPF-Tmem79-KO mouse to which $2.0 \times 10^6$ CFU of *S. epidermidis* or *S. lentus* had been applied showed no obvious induction of dermatitis. The results are shown in FIG. 8B.

From the results, it was suggested that only the specific bacteria excluding *S. epidermidis* and *S. lentus* were able to initiate the dermatitis.

Experimental Example 6

(Inflammation Suppressive Effect-1 of *S. cohnii*)

Next, the influence of other bacteria in SPF-Tmem79-KO mouse was verified.

Ampicillin (manufactured by NACALAI TESQUE, INC.) or fusidic acid (manufactured by Sigma-Aldrich Co. LLC.) was suspended in drinking water so as to be 200 mg/mL and the resultant drinking water was administered to the SPF-Tmem79-KO mouse, and the clinical scores were obtained with time.

Figure 9:
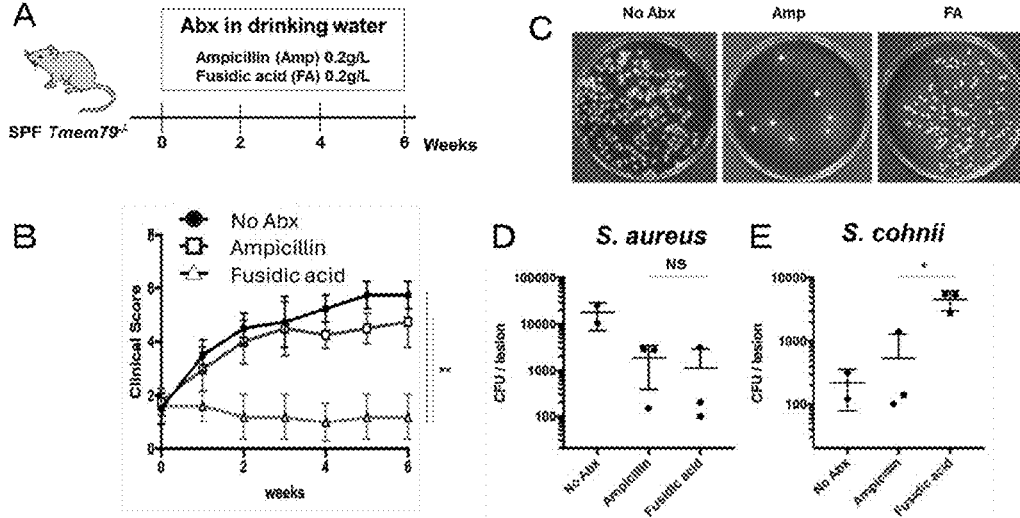
FIG. 9A is a schematic diagram showing an experimental flow.
FIG. 9B is a graph that indicates changes over time of clinical scores in the skins of SPF-Tmem79$^{-/-}$ mice inoculated with ampicillin (Amp) or fusidic acid (FA) being an antibiotic (ABx).
FIG. 9C shows photographs of culture media when bacteria collected from the skins were cultured in the culture media containing respective antibiotics.
FIGS. 9D and 9E are graphs each indicate the number of colonies of respective bacteria.

The degree of dermatitis was alleviated in the mouse to which fusidic acid had been administered, but the alleviation of the dermatitis was not observed in the mouse to which ampicillin had been administered (FIG. 9B).

Further, the sensitivity of *S. aureus* and *S. cohnii* to both antibiotics was verified by using the antibiotics. The proliferation of *S. aureus* was suppressed by any one of the ampicillin and the fusidic acid (FIGS. 9C and 9D). In addition, it was found that the proliferation of *S. cohnii* was significantly suppressed by the ampicillin, but the proliferation of *S. cohnii* was not suppressed by the fusidic acid (FIGS. 9C and 9E).

From these results, *S. cohnii* is sensitive to ampicillin but is resistant to fusidic acid, and the exacerbation of dermatitis is suppressed by the fusidic acid, and thus it is presumed that a bacterium that is sensitive to ampicillin and further resistant to fusidic acid, such as *S. cohnii* has an effect of suppressing the exacerbation of dermatitis.

Experimental Example 7

(Inflammation Suppressive Effect-2 of *S. cohnii*)

Figure 10:
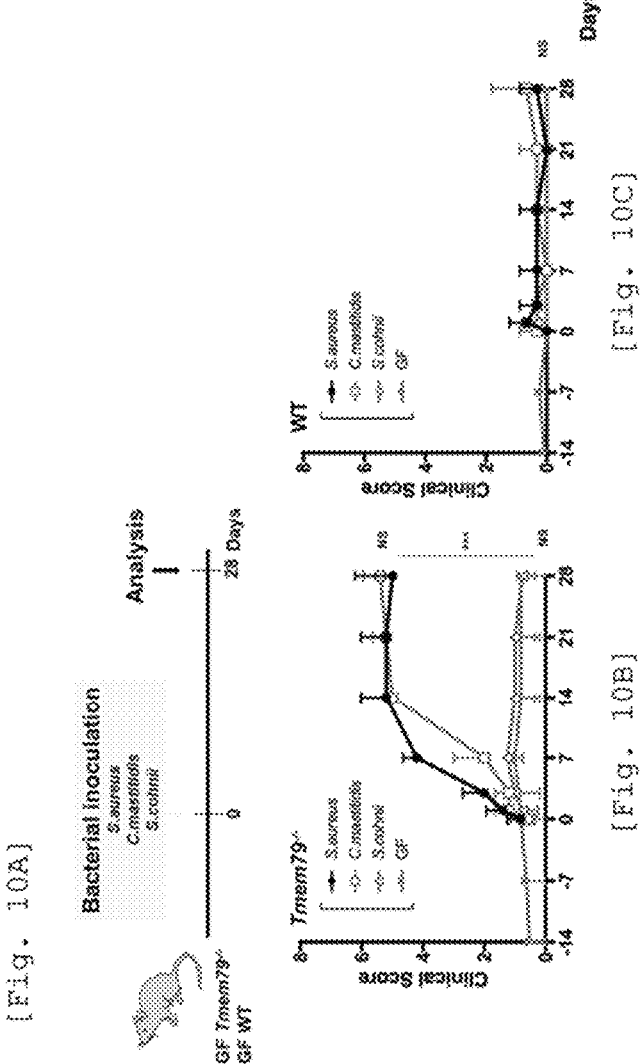
FIG. 10A is a schematic diagram showing an experimental flow.
FIGS. 10B and 10C are graphs each indicate changes over time of clinical scores in the skins of GF-Tmem79$^{-/-}$ mice or GF-WT mice inoculated with *S. aureus*, *Corynebacterium mastitidis* (*C. mastitidis*), or *S. cohnii*.

The amount of *S. aureus, C. mastitidis,* or *S. cohnii* in a culture medium was adjusted to $2.0 \times 10^6$ CFU, and the resultant culture medium was inoculated into a GF-Tmem79-KO mouse or a GF-WT mouse. Any one of the bacteria did not cause dermatitis in the GF-WT mouse (FIG. 10C), but in the GF-Tmem79-KO mouse, the *S. aureus* or *C. mastitidis* initiated dermatitis, while the *S. cohnii* did not cause dermatitis (FIG. 10B).

Experimental Example 8

(Preventive Effect of *Staphylococcus* Against Dermatitis)

The amount of *S. cohnii* or *S. epidermidis* in a culture medium was adjusted to $2.0 \times 10^6$ CFU, and the resultant culture medium was inoculated into a GF-Tmem79-KO mouse, and on the 14th day after the inoculation, *S. aureus* was inoculated into the mouse.

Figure 11:
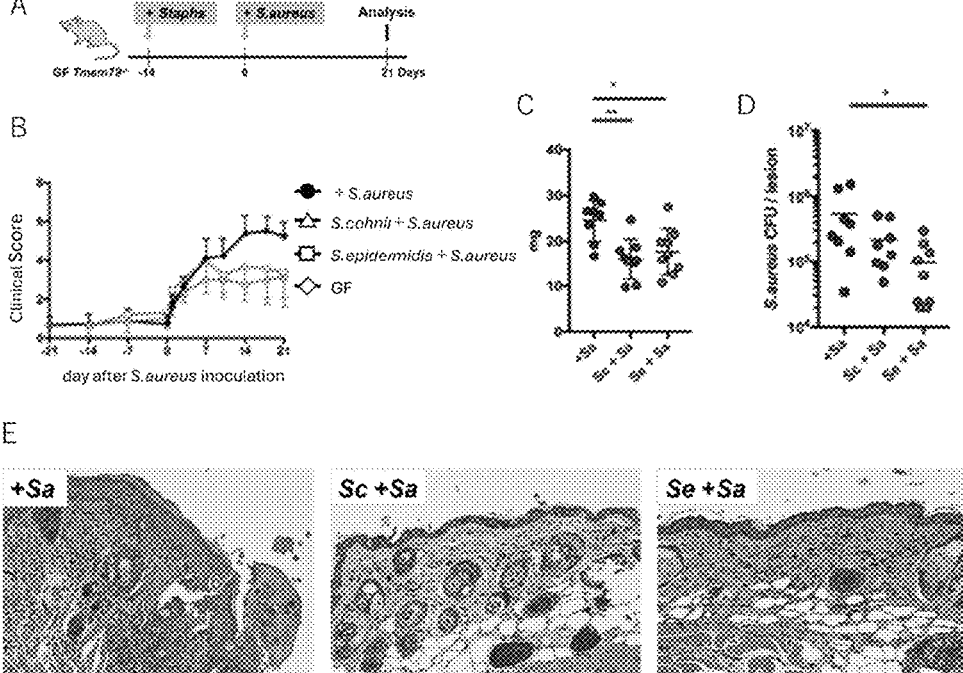
FIG. 11A is a schematic diagram showing an experimental flow.
FIGS. 11B to 11D are graphs each indicate changes over time of clinical scores in the skins of GF-Tmem79$^{-/-}$ mice inoculated with *S. cohnii* or *S. epidermidis* in advance and then inoculated with *S. aureus* on the 14th day after the inoculation of the *S. cohnii* or *S. epidermidis*, and weight of cervical lymph nodes (CLN) and amount of *S. aureus* on the 21st day after the inoculation of *S. aureus*.
FIG. 11E shows microscope images of pathological tissues of the histo-stained skins of respective mice. The image on the left is a microscope image of the mouse skin on the 21st day after the inoculation of *S. aureus*, the image in the middle is a microscope image of the mouse skin inoculated with *S. cohnii* prior to the inoculation of *S. aureus*, and the image on the left is a microscope image of the mouse skin inoculated with *S. epidermidis* prior to the inoculation of *S. aureus*.

According to the clinical scores, it was confirmed that preventive inoculation of *S. cohnii* or *S. epidermidis* suppressed the inflammation by *S. aureus* (FIG. 11B).

The cervical lymph node swelling on the 21st day after the inoculation of *S. aureus* was also suppressed by the preventive administration of *S. cohnii* or *S. epidermidis*, similarly as in the clinical scores (FIG. 11C).

In addition, there was no significant difference in the amount of *S. aureus* in each group during the same period (FIG. 11D).

Further, using the skin of each mouse, histopathologic examination was performed by hematoxylin-eosin (HE) staining. From the stained images, it was revealed that dermatitis was obviously suppressed by the preventive administration of *S. cohnii* or *S. epidermidis* (FIG. 11E).

Experimental Example 9

(Therapeutic Effect of *Staphylococcus* Against Dermatitis)

Further, the therapeutic effect of *Staphylococcus* on the dermatitis by *S. aureus* was verified.

Figure 12:
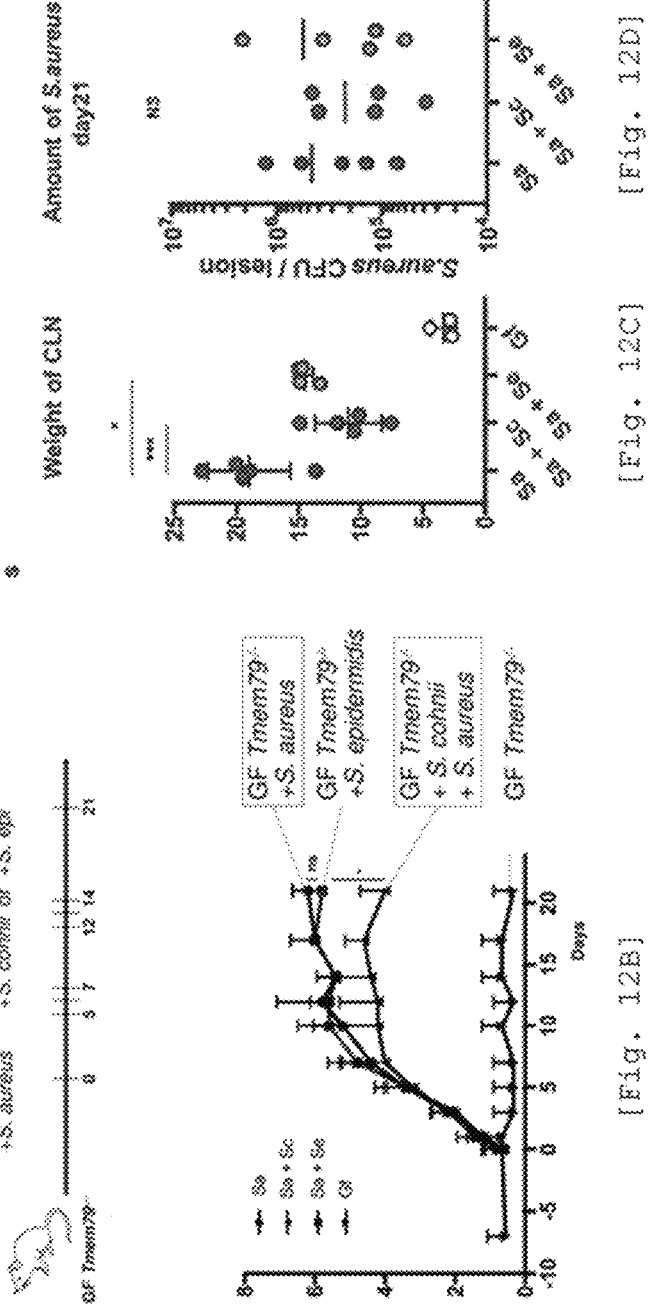
FIG. 12A is a schematic diagram showing an experimental flow.
FIG. 12B is a graph that indicates changes over time of clinical scores in the skins of GF-Tmem79$^{-/-}$ mice inoculated with *S. aureus* and then inoculated with *S. cohnii* or *S. epidermidis* on the 5, 6, 7, 12, 13, and 14th days after the inoculation of the *S. aureus*.
FIGS. 12C and 12D are graphs that indicate weight of cervical lymph nodes and amount of *S. aureus*, respectively on the 21st day after the inoculation of *S. aureus*.

The amount of *S. aureus* in a culture medium was adjusted to $2.0 \times 10^6$ CFU, and the resultant culture medium was inoculated into GF-Tmem79-KO mouse, and then the amount of *S. cohnii* or *S. epidermidis* in a culture medium was adjusted to $2.0 \times 10^6$ CFU, and the resultant culture medium was inoculated into the GF-Tmem79-KO mouse on the 5, 6, 7, 12, 13, and 14th day after the inoculation of *S. aureus*. The clinical scores were measured at each time point, and further the swelling of the cervical lymph node and the amount of *S. aureus* were confirmed on the 21st day after the inoculation of *S. aureus*. Similarly as in Experimental Example 8, it was found that the clinical scores were reduced (FIG. 12B), and further the swelling of the cervical lymph node was suppressed by the administration of *S. cohnii* (FIG. 12C). In addition, similarly, no apparent difference in the amount of *S. aureus* was observed (FIG. 12D).

Experimental Example 10

(Gene Expression Analysis by *S. cohnii*)

In order to examine the influence of *S. cohnii* or the like in the mice in the above Experimental Examples, RNA-sequencing analysis was performed by HiSeq (registered trademark, available from Illumina K.K.) with the use of the total RNAs extracted from the skin of a gnotobiotic Tmem79-KO mouse.

Figure 13:
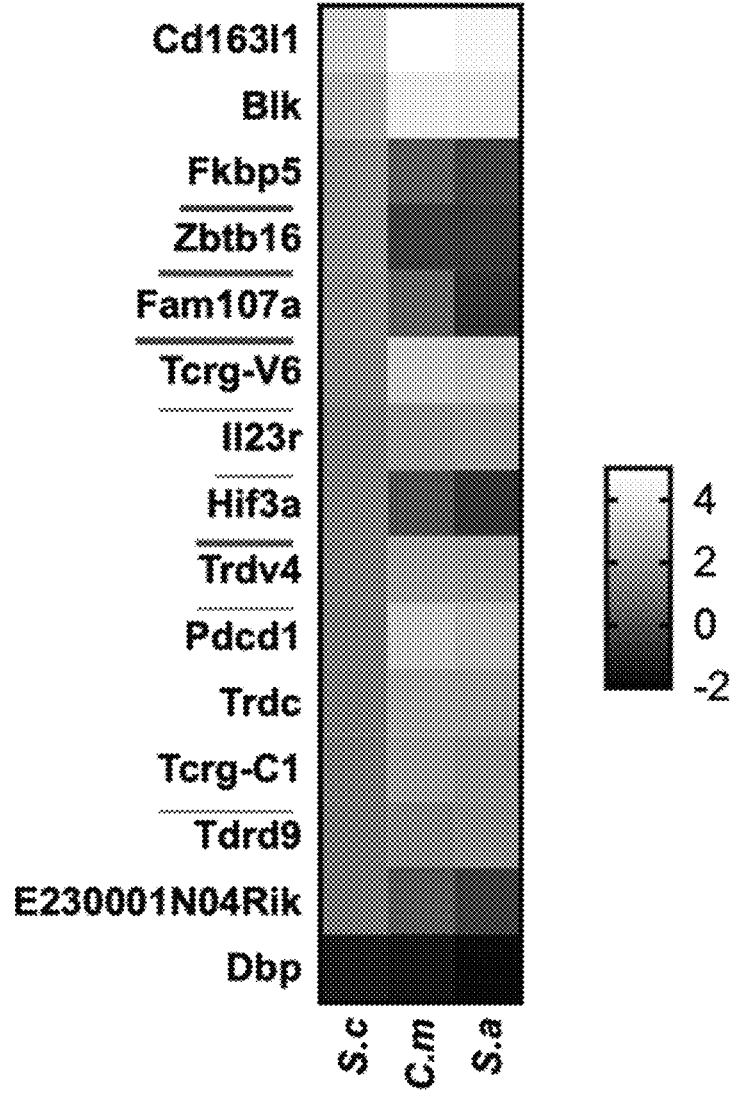
FIG. 13 shows results of RNA-sequencing analysis using the total RNA extracted from the skin of gnotobiotic Tmem79$^{-/-}$ mouse inoculated with *S. cohnii, C. mastitidis*, or *S. aureus*.

The ratio of the gene expression levels between each notobiate mouse prepared by using a GF-Tmem79-KO mouse and *S. aureus, C. masititis,* or *S. cohnii* and GF-Tmem79 is shown by log-fold change (FIG. 13).

In the gnotobiotic mice prepared by *S. cohnii*, 15 differentially-expressed genes (DEGs) were identified, and 5 genes among the 15 genes were genes of which the expression was *S. cohnii*-specifically enhanced. Further, it was able to be confirmed that the expression of a gene known as a glucocorticoid-responsive gene, such as Fkbp5, Zbtb16, Fam107a, or Hif3a was *S. cohnii*-specifically enhanced.

Figure 14:
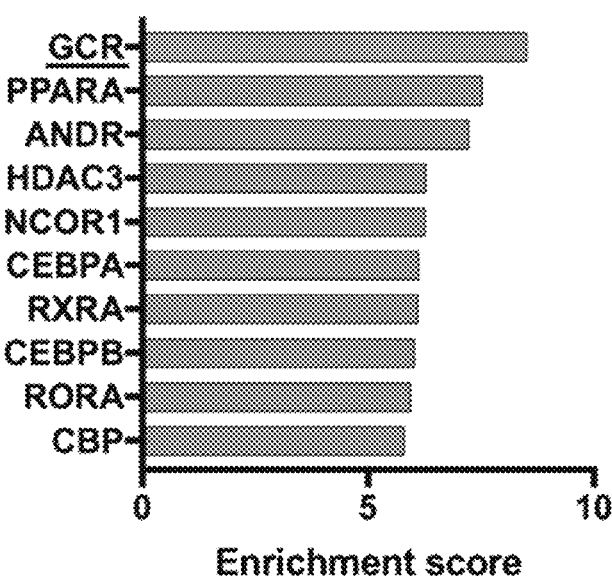
FIG. 14 shows results of enrichment analysis performed by using the total RNA extracted from the skin of gnotobiotic Tmem79$^{-/-}$ mouse inoculated with *S. cohnii, C. mastitidis*, or *S. aureus*.

Further, it was found that also in the results of enrichment analysis of transcription factors related to the differentially expressed genes, the gene expression of the glucocorticoid receptor (GCR) was strongest in the gnotobiotic mice prepared by *S. cohnii* (FIG. 14).

Figure 15:
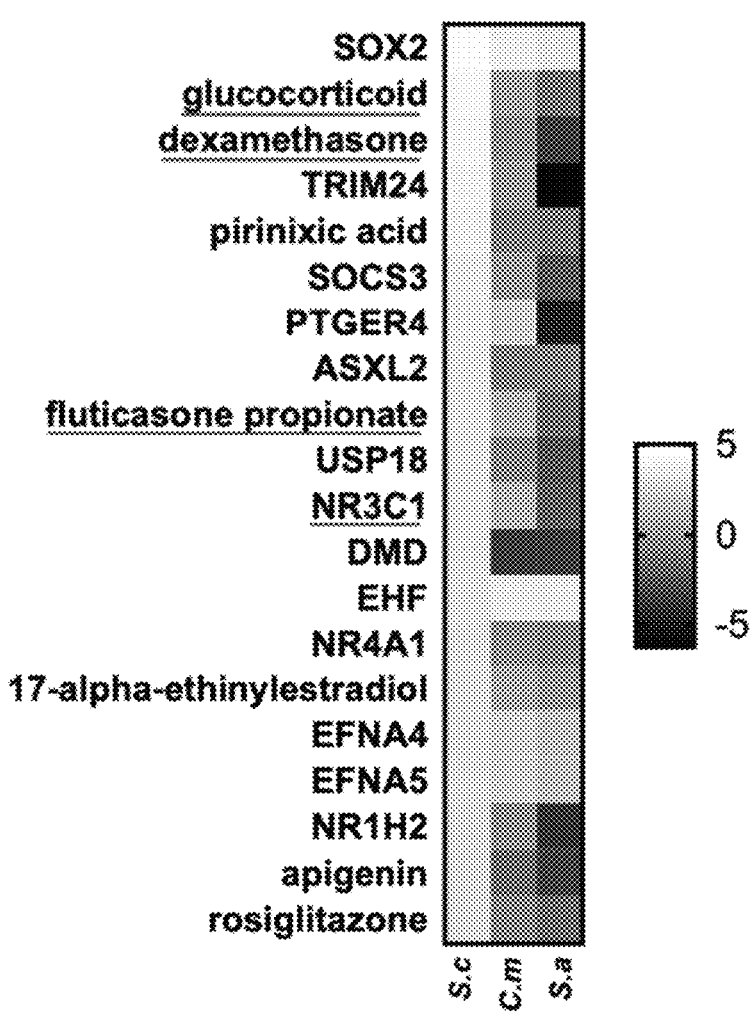
FIG. 15 shows results of gene expression cascade analysis (upstream analysis) using the total RNAs extracted from the skin of gnotobiotic Tmem79$^{-/-}$ mouse inoculated with *S. cohnii*.

In the RNA-sequencing analysis, in order to analyze the upstream gene that causes the expression of a specific differentially expressed gene in the gnotobiotic mice prepared by *S. cohnii*, gene expression cascade analysis (upstream analysis) was performed by using IPA (registered trademark, Ingenuity Pathway Analysis, available from Qiagen). The results are shown in FIG. 15.

As a result, a steroid such as glucocorticoid was specifically detected as the upstream of the gene expression pattern of *S. cohnii*. The glucocorticoid is a steroid hormone that has a strong anti-inflammatory action and a strong immunosuppressive action, and has a close relationship with the immune system.

Figure 16:
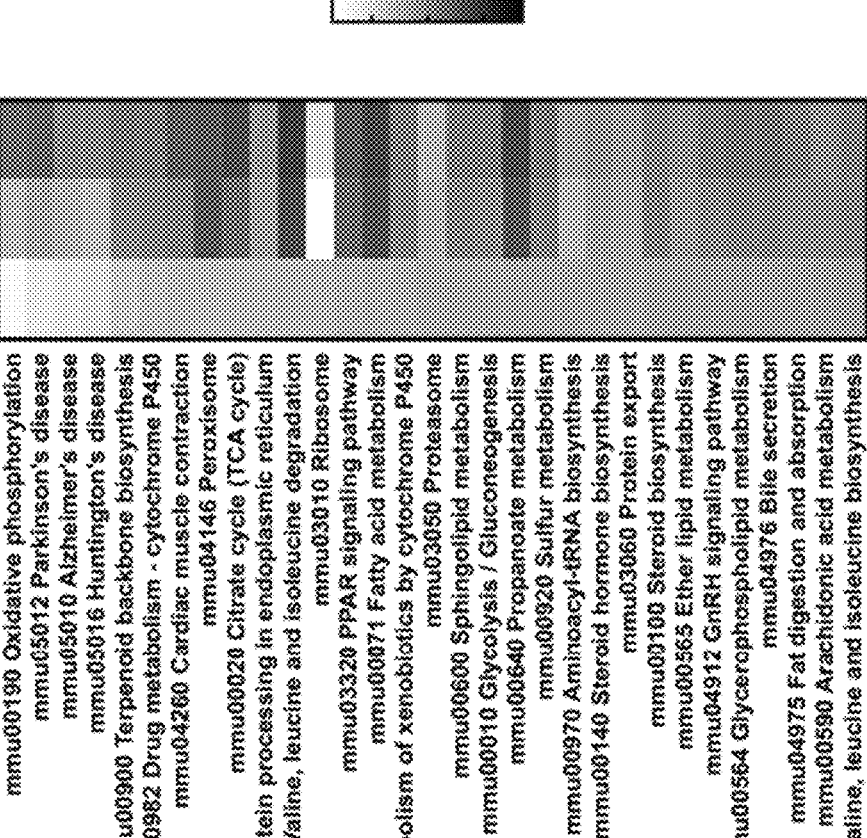
FIG. 16 shows results of pathway analysis using the RNA-sequencing analysis results that are results of Experimental Example 10 (FIG. 13).

Further, pathway analysis was performed by using the RNA-sequencing analysis data. In the gnotobiotic mouse by *S. cohnii*, it was found that the pathway of synthesis of a terpenoid (precursor of steroid) or CYP450 (involved in steroid metabolism) was enhanced (FIG. 16).

As described above, from the results of multiple gene expression analyses using gnotobiotic mice prepared by *S.*

*cohnii* or the like, it is suggested that *S. cohnii* may act suppressively against skin inflammation by promoting the immunity by glucocorticoid reaction.

Experimental Example 11

(Enhancement of Glucocorticoid Gene Expression)

The expression levels of three genes Fkbp5, Zbtb16, and Tsc22d3 that are known as glucocorticoid-responsive genes in the skins of gnotobiotic Tmem79-KO mouse using *S. aureus, S. cohnii, S. epidermidis*, and *S. lentus* were analyzed.

A skin sample of each mouse was homogenized by using NS-360D (available from Microtec Co., Ltd, Chiba, Japan), 2.2 mg/mL of proteinase K (Takara 9034) was added into the homogenized sample, the mixture was cultured at 55° C. for 10 minutes, the total RNA was extracted from the obtained culture, and the reverse transcription was performed by SuperScript (registered trademark) III First-Strand Synthesis System (available from Thermo Fisher Scientific) to obtain cDNA (for Zbtb16, Fkbp5, and Tsc22d3, a primer (non-public sequence) of Prime PCR SYBR (registered trademark) Green Assay (available from Bio-Rad Laboratories Inc.) was used, and for glyceraldehyde-3-phosphate dehydrogenase (GAPDH), forward: 5'-cctcgtcccgtagacaaaatg-3' (SEQ ID NO: 10) and reverse: 5'-tctccactttgccactgcaa-3' (SEQ ID NO: 11) were used as primers).

Each gene expression level was measured by performing qPCR with Thunderbird SYBR qPCR Mix (available from TOYOBO CO., LTD.) and LightCycler 480 II (available from Roche). Graphs, which were obtained by correcting the obtained measurement values with the gene dosage of GAPDH, are shown in FIGS. 17A to 17C.

Figure 17:
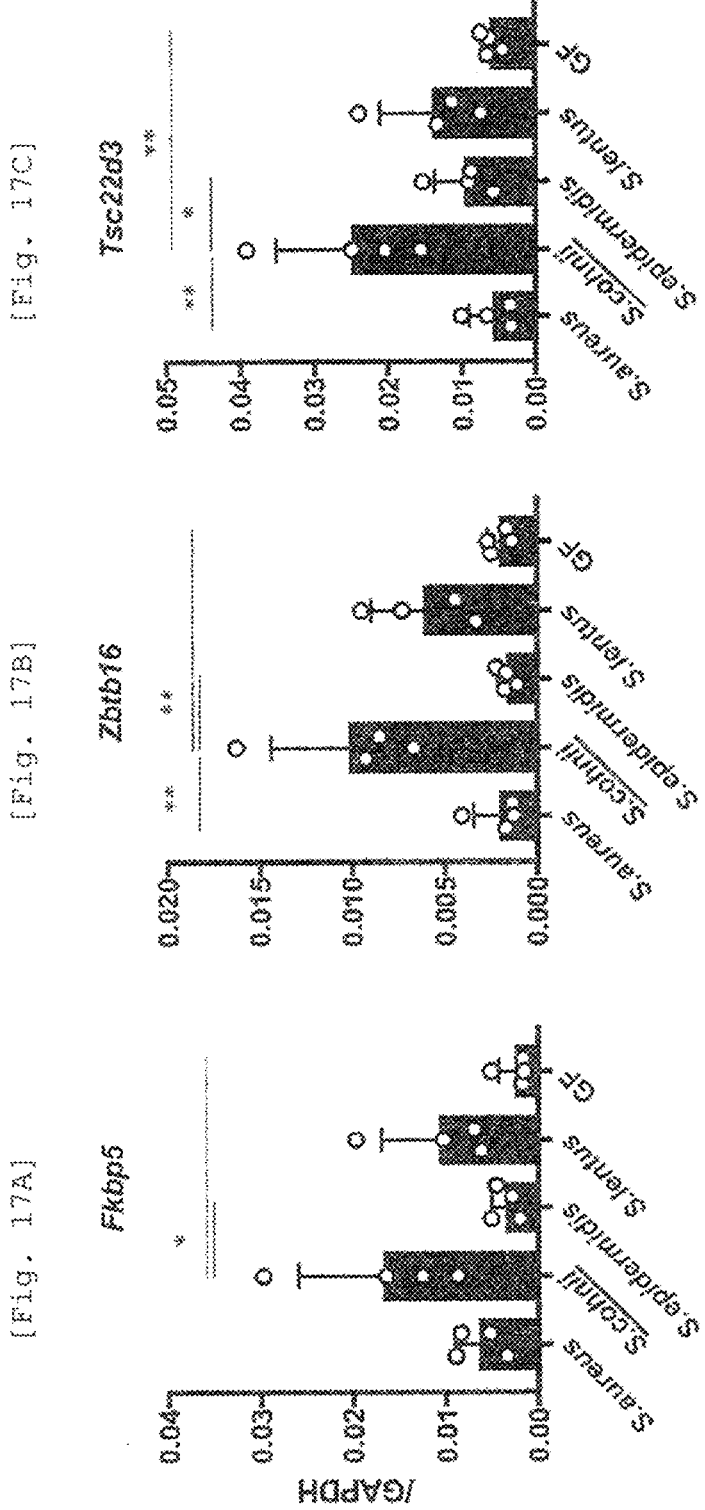
FIGS. 17A to 17C show results of measurement of the expression levels of glucocorticoid-responsive genes Fkbp5, Zbtb16, and Tsc22d3, respectively by reverse-transcribing the total RNAs extracted from the skins of gnotobiotic Tmem79$^{-/-}$ mice inoculated with *S. aureus, S. cohnii, S. epidermidis*, and *S. lentus*, and performing qPCR by using the obtained cDNAs.

As a result, it was confirmed that *S. cohnii*, and *S. lentus* enhanced the expression of these genes (FIGS. 17A to 17C).

Figure 18:
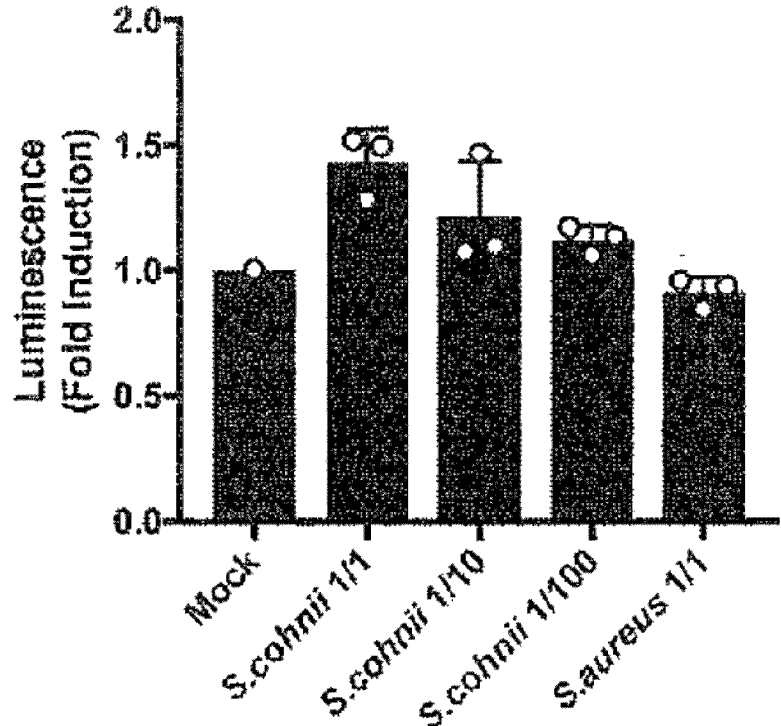
FIG. 18 shows results of GAL4 reporter assay performed by using *S. cohnii* or *S. aureus*.

As the reporter assay of the glucocorticoid receptor, the GAL4 reporter assay was performed as follows: the amount of *S. cohnii* or *S. aureus* was adjusted to an optical density at 600 nm (OD 600) of 0.6, the adjusted *S. cohnii* or *S. aureus* was added to a GAL4 reporter, Luciferase, a HEK293 cell line (cell strain for measurement of glucocorticoid receptor signaling pathway) in each well, the culture was conducted for 24 hours, and the amount of luminescence was measured by using ONE-Step luciferase assay system (#60690-1, available from BPS Bioscience Inc.). It can be understood that the glucocorticoid signaling pathway is activated by culturing the cells with the addition of *S. cohnii*. The results are shown in FIG. 18.

On the other hand, it was not able to be confirmed that the activity was enhanced in the case of *S. aureus*.

Experimental Example 12

(Inflammation Suppressive Effect of Newly Isolated Strain of *S. cohnii*)

In the above-described Experimental Examples, as the *S. cohnii*, a strain named BP-02848 isolated by the technique similar to that in Preparation Example 2 was used. In order to confirm that other strains of *S. cohnii* also have an effect similar to that of BP-02848, the following experiments were conducted by using *S. cohnii* strains newly isolated from the mouse skin, BP-02850, BP-02851, and BP-02852.

An imiquimod (IMQ)-induced model is known as the typical psoriasis-like dermatitis-induced model (van der Fits, et al., J Immunol. May 1, 2009, 182(9): 5836-45).

Onto the ears of a GF-WT mouse, imiquimod (product name: Beselna cream, manufactured by MOCHIDA PHAR- MACEUTICAL CO., LTD.) was applied at a dose of 50 mg per mouse once a day for 5 consecutive days. For the first 2 days, *S. cohnii* or *S. epidermidis* was inoculated at the same time onto the ears at a dose of $2.0 \times 10^7$ CFU per mouse once a day with a cotton swab.

Figure 19:
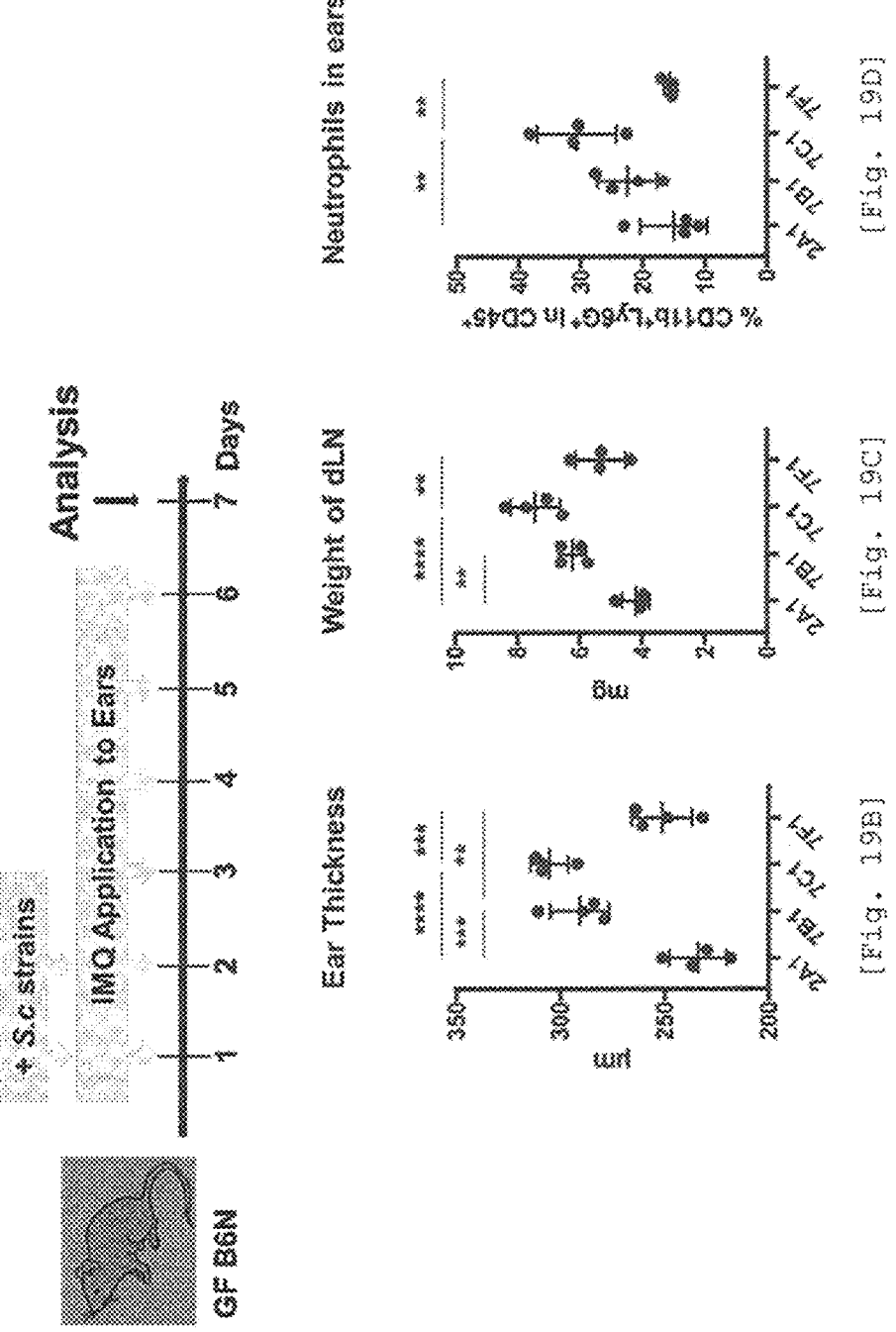
FIG. 19A is a schematic diagram showing an experimental flow.
FIGS. 19B to 19D show results of measurement of thickening of the ear, weight of lymph nodes (dLN), and the number of neutrophils by FACS of GF-WT (GF B6N) mice applied with imiquimod cream (IMQ), when 2A1 (deposited under Accession number: NITE BP-02848, the same is applied to the following drawings), which is an existing *S. cohnii* strain, and 7B1 (deposited under Accession number: NITE BP-02850, SEQ ID NO: 2, the same is applied to the following drawings), 7C1 (deposited under Accession number: NITE BP-02851, SEQ ID NO: 3, the same is applied to the following drawings), and 7F1 (deposited under Accession number: NITE BP-02852, the same is applied to the following drawings), which are newly-isolated *S. cohnii* strains, are inoculated into the mice, respectively.

The degree of the suppression of both of the ear swelling and the lymph node swelling and the degree of the reduction of neutrophils, by imiquimod, differed from one strain to another. The results are shown in FIGS. 19B to 19D.

Experimental Example 13

(Preventive Effect of Newly Isolated Strain of *S. cohnii* on Dermatitis Initiated by *S. aureus*)

Figure 20:
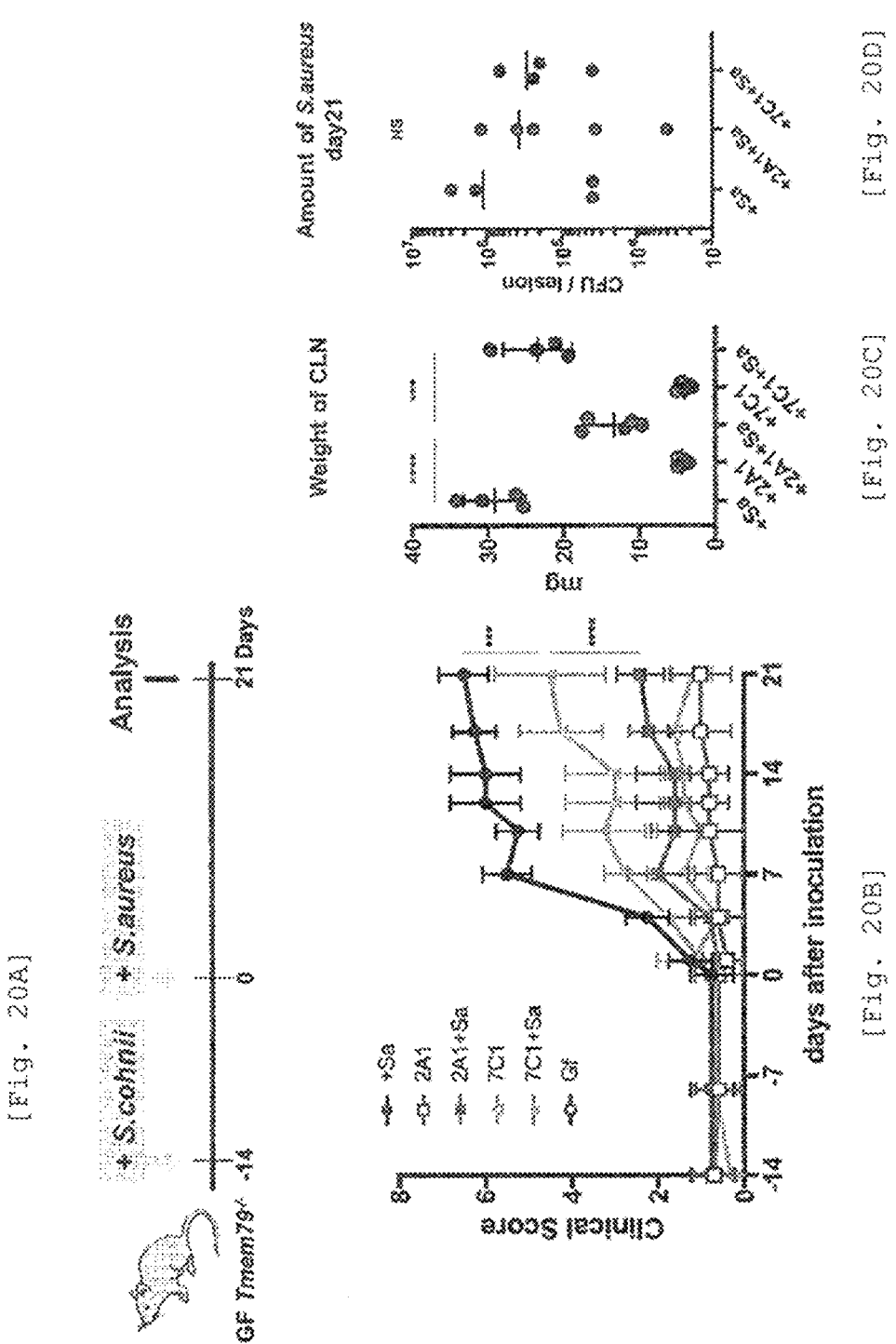
FIG. 20A is a schematic diagram showing an experimental flow.
FIG. 20B is a graph that indicates changes over time of clinical scores in the skins of gnotobiotic GF Tmem79$^{-/-}$ mice inoculated with 2A1 or 7C1 being a bacterium strain derived from *S. cohnii* and then inoculated with *S. aureus* on the 14th day after the inoculation of 2A1 or 7C1.
FIGS. 20C and 20D are graphs that indicate weight of cervical lymph nodes and amount of *S. aureus*, respectively on the 21st day after the inoculation of *S. aureus*.

Strains of *S. cohnii*, that is, BP-02848, and BP-02851 were inoculated into GF-Tmem79-KO mouse, respectively, and on the 14th day after the inoculation, a culture medium in which the amount of *S. aureus* had been adjusted to $2.0 \times 10^6$ CFU was inoculated into the mice. Considering the clinical scores, it was indicated that both strains of BP-02848 and BP-02851 had an amelioration effect on dermatitis, and further both strains suppressed cervical lymph node swelling in the mice (FIGS. 20B and 20C). In this regard, both of the clinical scores and the degree of cervical lymph node swelling differed from one strain to another.

However, on the 21st day after the inoculation of *S. aureus*, no apparent difference in the amount of *S. aureus* was observed in any of the mice (FIG. 20D).

Experimental Example 14

(Expression of Steroid Biosynthesis-Related Gene)

In Experimental Example 10, it was indicated that the gene expression of the glucocorticoid receptor (GCR) was strongest in the gnotobiotic mice prepared by *S. cohnii*.

Figure 21:
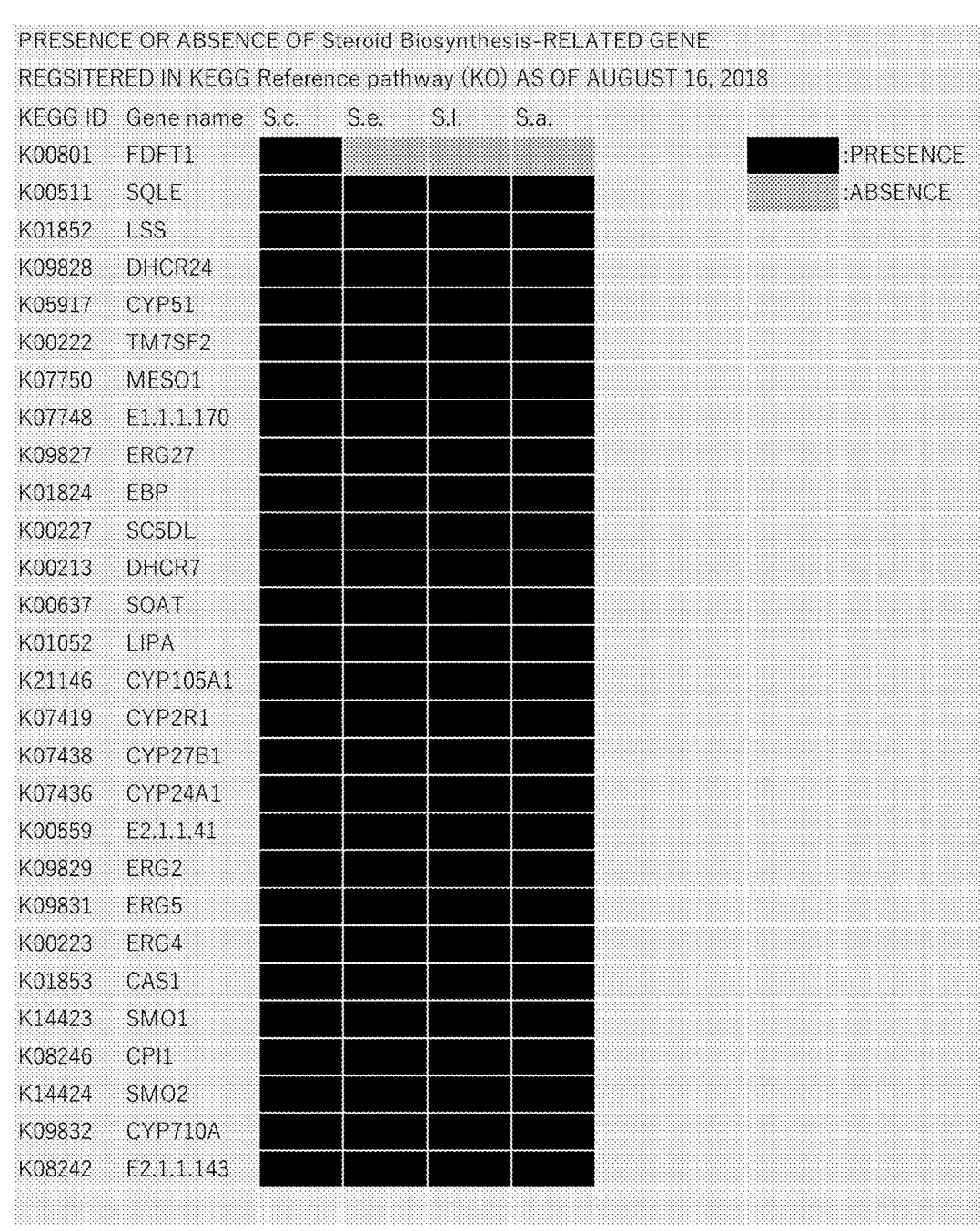
FIG. 21 shows analysis results of gene cascades of steroid biosynthesis-related genes.

In this regard, since glucocorticoid is one kind of steroids, the inventors were focused on the genes relating to steroid biosynthesis. For the entire genomes of *S. aureus, S. cohnii*, and *S. epidermidis* registered in National Center for Biotechnology Information (NCBI), the presence or absence of a steroid biosynthesis-related gene was determined and compared with each other. As a result, it was found that other enzyme genes were commonly expressed in the three bacteria, but squalene synthase (farnesyl-diphosphate farnesyltransferase (FDFT1) gene, KEGG ID: K00801) was expressed only in *S. cohnii* (FIG. 21).

According to the Kyoto Encyclopedia of Genes and Genomes (KEGG) Reference Pathway, a terpenoid skeleton is biosynthesized from the glycolytic pathway, squalene is induced through the effect of FDFT1, and then biologically active substances having various steroid skeletons are synthesized in the downstream. In other words, FDFT1 is one of the key genes of a steroid biosynthesis cascade, it is considered that a biologically active substance having a steroid skeleton cannot be synthesized from the glucose metabolism without the FDFT1, and a biologically active substance exerting an anti-inflammatory effect is not produced.

As described above, it is considered that a cascade for producing a biologically active substance that exerts an anti-inflammatory effect is initiated by the squalene produced by *S. cohnii*, and an inflammation relief action by *S. cohnii* is induced.

Experimental Example 15

(Inflammation Suppressive Effect by Squalene)

In order to support the results of Experimental Example 14, it was examined whether the administration of squalene suppressed the inflammation similarly to *S. cohnii*, or whether the administration of mifepristone inhibited the inflammation suppressive effect.

Imiquimod (Beselna cream, manufactured by MOCHIDA PHARMACEUTICAL CO., LTD.) was applied onto the ears of a GF-WT mouse at a dose of 50 mg per mouse once a day for 5 consecutive days.

For the first 3 days, *S. cohnii* was inoculated onto the ears at a dose of $2.0 \times 10^7$ CFU per mouse once a day with a cotton swab, or squalene (S3626-10ML, manufactured by Sigma-Aldrich Co. LLC.) was applied onto the ears of the mouse at a dose of 200 μl per mouse once a day for 5 consecutive days. Further, in another group of mice, mifepristone (M8046-1G, manufactured by Sigma-Aldrich Co. LLC) was administered to the mice freely at 210 μg/mL in drinking water during the experimental period.

It was able to be confirmed that imiquimod-initiated inflammation (ear swelling and lymph node swelling) was suppressed by the inoculation of *S. cohnii*, and further the suppression was inhibited by mifepristone. In addition, similarly, the suppression of imiquimod-initiated inflammation, the degree of which was almost the same as that of *S. cohnii*, was observed also in the mice to which squalene had been applied instead of the inoculation of *S. cohnii*, and the inhibition of suppressive effect by mifepristone was similarly confirmed. The results are shown in (FIGS. 22B and 22C).

Experimental Example 16

(Inflammation Suppressive Effect by Human-Derived *S. cohnii*)

It was recognized that the mouse-derived *S. cohnii* strain, BP-02848 used in the above had a similar anti-inflammatory effect also on a human, by the analysis of the present inventors.

In view of this, subsequently, it was verified whether a human-derived *S. cohnii* strain had an anti-inflammatory effect similarly.

Isolation of *S. cohnii* from the skin of a healthy volunteer was performed on the basis of the protocol approved by No. H27-1 "Analysis of human skin microbiota" at RIKEN. Specifically, the skin in the forehead of a healthy volunteer was scraped with a cotton swab immersed in PBS, the substance adhered to the cotton swab was re-dispersed in 1 mL of PBS to obtain a bacterial liquid, the bacterial liquid was applied onto mannitol salt agar (05236, manufactured by Nissui Pharmaceutical Co., Ltd.), and the culture was performed, and a human-derived *S. cohnii* strain, BP-02853 was identified on the basis of the analysis of 16SrDNA on the isolated strain obtained from the formed colony.

The human-derived *S. cohnii* strain, BP-02853 was administered to a SPF-WT mouse, and the anti-inflammatory effect was examined.

Imiquimod (Beselna cream, manufactured by MOCHIDA PHARMACEUTICAL CO., LTD.) was applied onto the ears of a SPF-WT mouse at a dose of 50 mg per mouse once a day for 5 consecutive days.

For the first 3 days, *S. cohnii* (mouse-derived strain, BP-02848, or human-derived strain, BP-02853) or *S. epidermidis* was inoculated onto the ears at a dose of $2.0 \times 10^7$ CFU per mouse once a day with a cotton swab.

By the inoculation of *S. cohnii* strain, BP-02853, the degree of inflammation and the lymph node swelling were suppressed almost the same degree as that of the BP-02848 (FIGS. 23B and 23C).

Experimental Example 17

(*S. aureus*-Dependent Inflammation Suppressive Effect by Combination of Human-Derived *S. cohnii* and *S. epidermidis*)

Into GF-Tmem79-KO mouse, *S. aureus* was inoculated at a dose of $2.0 \times 10^7$ CFU per mouse. On the 5, 6, 7, 12, 13, and 14th day after the inoculation, 2) only *S. cohnii,* 3) only *S. epidermidis*, and 3) *S. cohnii* and *S. epidermidis* were inoculated into the mice, respectively at a dose of $2.0 \times 10^7$ CFU per mouse (*S. cohnii* and *S. epidermidis* were each inoculated at a dose of $2 \times 10^6$ CFU per mouse, that is, $4 \times 10^6$ CFU per mouse in total) (FIG. 24A). In this regard, 1) was a positive control, and into which only *S. aureus* was inoculated, and 5) the non-inoculated mouse was a negative control, and into which none of the bacteria had been inoculated.

According to the clinical scores, it was confirmed that in the mice into which *S. cohnii* or *S. epidermidis* had been inoculated alone, the inflammation by *S. aureus* was suppressed. Further, it was confirmed that in the mice into which *S. cohnii* and *S. epidermidis* had been inoculated in combination, the inflammation by *S. aureus* was further suppressed as compared with the mice into which the bacteria each had been inoculated alone (FIG. 24B).

In addition, the cervical lymph node swelling on the 21st day after the inoculation of *S. aureus* was also suppressed by the preventive administration of *S. cohnii* or *S. epidermidis*, similarly as in the clinical scores (FIG. 24C).

Experimental Example 18

(*S. aureus*-Dependent Inflammation Preventive Effect by Combination of Human-Derived *S. cohnii* and *S. epidermidis*)

Only *S. cohnii*, only *S. epidermidis*, and combination of *S. cohnii* and *S. epidermidis* each at a dose of $2 \times 10^6$ CFU per mouse were inoculated in the skins of GF-Tmem79-KO mouse, respectively (*S. cohnii* and *S. epidermidis* were each inoculated at a dose of $2 \times 10^6$ CFU per mouse, that is, $4 \times 10^6$ CFU per mouse in total). At two weeks after the inoculation, *S. aureus* was inoculated in the skins of the GF-Tmem79-KO mouse at a dose of $2 \times 10^6$ CFU per mouse. The clinical scores obtained from the results observed with time are shown in FIG. 25A, and the weight of the cervical lymph node on the 21st day after the inoculation of *S. aureus* is shown in FIG. 25B.

According to the clinical scores, it was confirmed that in the mice into which *S. cohnii* or *S. epidermidis* had been inoculated alone in advance and the mice into which *S. cohnii* and *S. epidermidis* had been inoculated in combination in advance, the inflammation by *S. aureus* was suppressed (FIG. 25A).

In addition, the cervical lymph node swelling on the 21st day after the inoculation of *S. aureus* was also suppressed by the inoculation of *S. cohnii* or *S. epidermidis* in advance, similarly as in the clinical scores, and further the cervical lymph node swelling was further suppressed in the mice into which *S. cohnii* and *S. epidermidis* had been inoculated in combination in advance, as compared with the mice into which the bacteria each had been inoculated alone (FIG. 25B).

Experimental Example 19

(Change in Amount of Bacteria by Combination of Human-Derived *S. cohnii* and *S. epidermidis*)

Into GF-Tmem79-KO mouse, only *S. aureus*, combination of *S. aureus* and *S. cohnii*, combination of *S. aureus* and *S. epidermidis*, and combination of *S. aureus, S. cohnii*, and *S. epidermidis* were inoculated, respectively at a dose of $2.0\times10^7$ CFU per mouse, and the amount of bacteria was measured on the 21st day after the inoculation. It was found that a significant difference in the amount of *S. aureus* was not observed in the mice into which combination of *S. aureus* and *S. cohnii*, and combination of *S. aureus* and *S. epidermidis* had been inoculated, respectively, as compared with the amount of *S. aureus* in the mice into which only *S. aureus* had been inoculated, but the amount of *S. aureus* was significantly reduced in the mice into which *S. cohnii* and *S. epidermidis* had been inoculated together with *S. aureus* (FIG. 26A). In this regard, there was no difference in the total amount of the bacteria including *S. aureus, S. cohnii*, and *S. epidermidis* among all of the mice (FIG. 26B). Further analysis revealed that the proportion of *S. aureus* was significantly lower in the mice into which *S. cohnii* and *S. epidermidis* had been inoculated together with *S. aureus*, as compared with that in the mice inoculated with other staphylococci (FIG. 26C). In this regard, a so much difference in the amount of *S. aureus* was not observed between the mice into which only *S. cohnii* or *S. epidermidis* had been inoculated together with *S. aureus* and the mice into which only *S. aureus* had been inoculated.

Experimental Example 20

(FACS Analysis of Skin)

In order to analyze the effect of local steroid metabolism of *S. cohnii*, mouse-derived *S. cohnii* (2A1), mouse-derived *S. cohnii* (7C1), human-derived *S. cohnii* (10B1), and mouse-derived *S. aureus* (1D1) were inoculated in the backs of 8-week old germ-free B6N WT mice, respectively at a dose of $2\times10^6$ CFU per mouse. Each skin was collected at 4 weeks after the administration, and FACS analysis was performed on the T cells. FIG. 27 shows the amount of bacteria and the results of FACS analysis in each mouse.

In the cases of *S. cohnii* (2A1, 7C1, and 10B1), IL-17A-producing T cells being inflammatory immune cells were not induced, but on the other hand, in the case of *S. aureus* (1D1), IL-17A-producing T cells were induced even in the wild-type mice. Further, the induction of Treg cells represented by Foxp3+CD4 T cells did not change in the cases of *S. cohnii*, and was reduced in the case of *S. aureus*.

From these points, the induction of inflammatory T cells was not observed in the wild-type mice into which *S. cohnii* had been inoculated, and it was considered that the inflammation suppressive effect by *S. cohnii* was a mechanism different from that of the induction of Treg cells.

Experimental Example 21

(Detection of Glucocorticoid −1)

In order to further perform detailed analysis of corticoid, mouse-derived *S. cohnii* (2A1), mouse-derived *S. cohnii* (7C1), human-derived *S. cohnii* (10B1), and mouse-derived *S. aureus* (1D1) were inoculated into 8-week old germ-free B6N WT mice, respectively at a dose of $2\times10^6$ CFU per mouse, and GC-MS fatty acid analysis was performed by using the back skins and neck skins on the 28th day after the inoculation. Corticosterone was detected more significantly in a large mount in both of the back and the neck of the mice into which *S. cohnii*, in particular, mouse-derived *S. cohnii* (2A1) had been inoculated, as compared with that in the non-treated mice. However, a significant difference in the amount of the progesterone being a precursor of corticosterone was not observed in both of the back and the neck of all of the mice (FIG. 28).

Experimental Example 22

(Detection of Glucocorticoid −2)

Mouse-derived *S. cohnii* (2A1) and mouse-derived *S. cohnii* (7C1) were inoculated in the necks of Tmem79-KO mouse, respectively at a dose of $2\times10^6$ CFU per mouse, and GC-MS fatty acid analysis was performed on the neck skins on the 28th day after the inoculation in a similar manner as in the Experimental Example 21. The results of the analysis performed on the corticosterone and the progesterone, in a similar manner as in Experimental Example 21 are shown in FIG. 29. The corticosterone was more significantly detected in a large amount in the necks of the mice into which mouse-derived *S. cohnii* (2A1) had been inoculated, as compared with that in the non-treated mice. However, a significant difference in the amount of the progesterone being a precursor of corticosterone was not observed in all of the mice (FIG. 29).

(Consideration)

In the present study, it has been revealed from the results of the above-described Experimental Examples and the like, that *S. cohnii, S. epidermidis*, or the like, which is one species of skin normal bacteria, has preventive and therapeutic effects against dermatitis. Further, it has been found that these bacteria act on the host and enhance the activity of the glucocorticoid-responsive genes in the skin of the host, and in particular, squalene synthase is specifically expressed in the bacteria that have a suppressive effect on dermatitis.

On the basis of the action mechanism as described above, it is considered that the exacerbation of dermatitis can be controlled by specific skin normal bacteria such as *S. cohnii*, and this may lead to the drug discovery for the treatment, amelioration, or prevention of dermatitis, to the development of a quasi drug or cosmetics for the skin, and to the development of a new treatment method.

The invention claimed is:

1. A pharmaceutical A pharmaceutical composition, for suppressing dermatitis comprising as active components a bacterial cell of a bacterium sensitive to ampicillin; wherein a 16S rDNA gene sequence of the bacterium sensitive to ampicillin is a sequence represented by SEQ ID NO. 5, or a sequence having at least 99% or more sequence identity to the sequence represented by SEQ ID NO. 5;

the bacterium sensitive to ampicillin is a live bacterium;

the bacterium is *Staphylococcus cohnii* isolated from human skin;

wherein the composition is formulated as an external preparation in order to apply or paste the pharmaceutical composition for the administration; and wherein the pharmaceutical composition comprises at least one of a pharmaceutically acceptable carrier or an additive agent, wherein the pharmaceutically acceptable carrier and the additive are selected from the group consisting of an excipient, a suspending agent, an isotonizing agent, an emulsifying agent.

2. The pharmaceutical composition according to claim 1, wherein the bacterium sensitive to ampicillin is a fusidic acid-resistant bacterium.

3. The pharmaceutical composition according to claim 1, wherein the bacterium sensitive to ampicillin is bacteria deposited under an Accession number NITE BP-02853.

* * * * *